US 7,241,909 B2

(12) United States Patent
DeLuca et al.

(10) Patent No.: US 7,241,909 B2
(45) Date of Patent: Jul. 10, 2007

(54) 19,26,27-TRINOR-1α,25-DIHYDROXYVITAMIN D₃ COMPOUNDS

(75) Inventors: Hector F. DeLuca, Deerfield, WI (US);
Pawel Grzywacz, Madison, WI (US);
Lori A. Plum, Arena, WI (US);
Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/416,401

(22) Filed: May 2, 2006

(65) Prior Publication Data

US 2006/0264410 A1    Nov. 23, 2006

Related U.S. Application Data

(60) Provisional application No. 60/677,232, filed on May 3, 2005.

(51) Int. Cl.
*C07D 401/00*    (2006.01)
*A61K 31/59*    (2006.01)

(52) U.S. Cl. ..................... 552/653; 514/167
(58) Field of Classification Search ........... 514/167; 552/653
See application file for complete search history.

(56) References Cited

U.S. PATENT DOCUMENTS

| | | | |
|---|---|---|---|
| 4,666,634 A | 5/1987 | Miyamoto et al. | |
| 5,086,191 A | 2/1992 | DeLuca et al. | |
| 5,536,713 A | 7/1996 | Deluca et al. | |
| 5,585,369 A | 12/1996 | DeLuca et al. | |
| 5,843,928 A | 12/1998 | Deluca et al. | |
| 5,877,168 A * | 3/1999 | Miyamoto et al. | 514/167 |
| 5,945,410 A | 8/1999 | DeLuca et al. | |
| 6,127,559 A | 10/2000 | DeLuca et al. | |
| 6,392,071 B1 | 5/2002 | DeLuca et al. | |
| 6,537,981 B2 | 3/2003 | DeLuca et al. | |
| 6,566,352 B1 | 5/2003 | DeLuca et al. | |
| 6,579,861 B2 * | 6/2003 | DeLuca et al. | 514/167 |
| 6,627,622 B2 | 9/2003 | DeLuca et al. | |
| 6,806,262 B2 * | 10/2004 | DeLuca et al. | 514/167 |
| 6,992,074 B2 * | 1/2006 | DeLuca et al. | 514/167 |
| 2004/0220418 A1 | 11/2004 | DeLuca et al. | |

OTHER PUBLICATIONS

Sicinski et al. (J. Med. Chem., 1998, 41, 4662,-4674).*
International Search Report dated Nov. 27, 2006 for PCT/US2006/016875.
Baggiolini, et al., "Stereocontrolled Total Synthesis of 1α,25-Dihydroxyergocalciferol and 1α,Dihydroxyergocalciferol," J. Org. Chem. 51, 3098 (1986).
Daniewski, et al., "A Novel Silylcopper Catalyst for the Reductive Bromination of Hajos Dione. Improved Preparation of a CD Synthon for the Synthesis of Vitamin D," J. Org. Chem. 66, 626-628 (2001).
Mascarenas, et al., "Studies of the Synthesis of Side-Chain Hydroxylated Metabolites of Vitamin D. 3. Synthesis of 25-Ketovitamin D₃ and 25-Hydroxyvitamin D₃," J. Org. Chem. 51, 1269 (1986).
Posner, et al., "2-Fluoroalkyl A-Ring Analogs of 1,25-Dihydroxyvitamin D₃-Stereocontrolled Total Synthesis via Intramolecular and Intermolecular Diels-Alder Cycloadditions. Preliminary Biological Testing," J. Org. Chem. 60, 4617 (1995).
Lythgoe, et al., "Calciferol and its Relatives. Part 22. A Direct Total Synthesis of Vitamin D₂ and Vitamin D₃ ," J. Chem. Soc. Perkin Trans. I, N6, 590 (1978).
Lythgoe, "Synthetic Approaches to Vitamin D and its Relatives," Chem. Soc. Rev. 9, 449 (1983).
Mincione, et al., "Improved Conversion of Vitamin D₂ into the Windaus Ketone and its Regioselective Hydroxylation via Organoboranes at $C_{26}$," Synth. Commun 19, 723 (1989).
Miyamoto, et al., "Synthetic Studies of Vitamin D Analogues. XIV. Synthesis and Calcium Regulating Activity of Vitamin D₃ Analogues Bearing a Hydroxyalkoxy Group at the 2β—Position," Chem. Pharm. Bull. 41(6), 1111 (1993).
Nishii, et al., "The Development of Vitamin D₃ Analogues for the Treatment of Osteoporosis," Osteoporosis Int. Suppl. 1, 190 (1993).

(Continued)

*Primary Examiner*—Sabiha N. Qazi
(74) *Attorney, Agent, or Firm*—Foley & Lardner LLP

(57) ABSTRACT

Compounds of formula 1 are provided where $X^1$, $X^2$, and $X^3$ are independently selected from H or hydroxy protecting groups, and $R^1$ and $R^2$ have the definitions provided herein. Such compounds may be used in preparing pharmaceutical compositions and are useful in treating a variety of biological conditions

12 Claims, 8 Drawing Sheets

OTHER PUBLICATIONS

Okano, et al., "Regulatory Activities of 2β-(3-Hydroxypropoxy) -1$_\alpha$, 25-Dihydroxy-Vitamin D$_3$, a Novel Synthetic Vitamin D$_3$ Derivative, on Calcium Metabolism," Biochem. Biophys. Res. Commun. 163(3), 1444 (1989).

Ostrem, et al., "24- and 26-homo-1,25-dihydroxyvitamin D$_3$: Preferential activity in inducing differentiation of human leukemia cells HL-60 in vitro," Proc. Natl. Acad. Sci. USA, 84, 2610 (1987).

Perlman, et al., "1$_\alpha$, 25-Dihydroxy-19-Nor-Vitamin D$_3$, a Novel Vitamin D-related Compound with Potential Therapeutic Activity," Tetrahedron Lett. 31(13), 1823 (1990).

Perlman et al., "Novel Synthesis of 19-Nor-Vitamin D Compounds," Tetrahedron Lett. 32(52), 7663 (1991).

Peterson, et al., "Studies of the Ketone Obtained from the Ozonolysis of Vitamin D. Molecular Mechanics Calculations for It and Related Hydrindanones," J. Org. Chem. 51, 1948 (1986).

Posner, et al., "Stereocontrolled Total Synthesis of Calcitriol Derivatives: 1,25-Dihydroxy-2-(4'-hydroxybutyl)vitamin D$_3$ Analogs of an Osteoporosis Drug," J. Org. Chem. 59, 7855 (1994).

Sardina, et al., "Studies on the Synthesis of Side-Chain Hydroxylated Metabolites of Vitamin D. 2. Stereocontrolled Synthesis of 25-Hydroxyvitamin D$_2$," J. Org. Chem. 51, 1264 (1986).

Sicinski, R.R., et al., "New 1$_{60}$ ,25-Dihydroxy-19-norvitamin D$_3$ Compounds of High Biological Activity: Synthesis and Biological Evaluation of 2-Hydroxymethyl, 2-Methyl, and 2-Methylene Analogues," J. Med. Chem., 41, 4662-4674 (1998).

Toh et al., "Studies on a Convergent Route to Side-Chain Analogues of Vitamin D: 25-Hydroxy-23-oxavitamin D$_3$," J. Org. Chem. 48, 1414 (1983).

* cited by examiner

19,26,27-TRINOR-1α,25-DIHYDROXYVITAMIN D₃ COMPOUNDS

FIELD OF THE INVENTION

This invention relates to vitamin D compounds, and more particularly to 19,26,27-trinor-1α,25-dihydroxyvitamin D₃ compounds such as 2α-methyl-19,26,27-trinor-(20S)-1α,25-dihydroxyvitamin D₃ ("P10"), 2β-methyl-19,26,27-trinor-(20S)-1α,25-dihydroxyvitamin D₃ ("T-74"), and 2-methylene-19,26,27-trinor-(20S)-1α, 25-dihydroxyvitamin D₃ ("BM"), and to pharmaceutical formulations that include these compounds or mixtures thereof. The invention also relates to the use of P10, T-74, and BM, salts thereof, and mixtures thereof in the preparation of medicaments for use in treating various diseases.

BACKGROUND OF THE INVENTION

The natural hormone, 1α,25-dihydroxyvitamin D₃ (also referred to as 1α,25-dihydroxycholecalciferol and calcitriol) and its analog in the ergosterol series, i.e., 1α,25-dihydroxyvitamin D₂, are known to be highly potent regulators of calcium homeostasis in animals and humans, and their activity in cellular differentiation has also been established, Ostrem et al., *Proc. Natl. Acad. Sci. USA*, 84, 2610 (1987). Many structural analogs of these metabolites have been prepared and tested, including 1α-hydroxyvitamin D₃, 1α-hydroxyvitamin D₂, various side chain homologated vitamins, and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies. The structure of 1α,25-dihydroxyvitamin D₃ and the numbering system used to denote the carbon atoms in this compound are shown below.

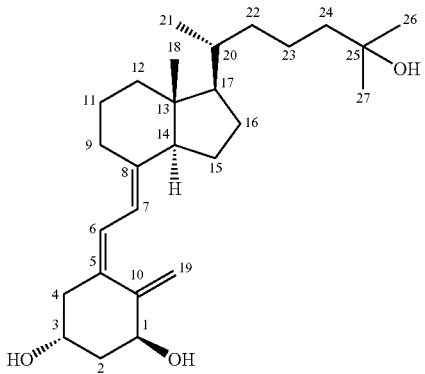

1α,25-Dihydroxyvitamin D₃=1α,25-Dihydroxycholecalciferol=Calcitriol

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin D₃) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., *Tetrahedron Lett*. 31, 1823 (1990); Perlman et al., *Tetrahedron Lett*. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin D₃ have been described and examined by the Chugai group as potential drugs for osteoporosis and as antitumor agents. See also Okano et al., *Biochem. Biophys. Res. Commun*. 163, 1444 (1989). Other 2-substituted (with hydroxyalkyl, e.g., ED-120, and fluoroalkyl groups) A-ring analogs of 1α,25-dihydroxyvitamin D₃ have also been prepared and tested (Miyamoto et al., *Chem. Pharm. Bull*. 41, 1111 (1993); Nishii et al., *Osteoporosis Int. Suppl*. 1, 190 (1993); Posner et al., *J. Org. Chem*. 59, 7855 (1994), and *J. Org. Chem*. 60, 4617 (1995)).

Various 2-substituted analogs of 1α,25-dihydroxy-19-nor-vitamin D₃ have also been synthesized, i.e. compounds substituted at the 2-position with hydroxy or alkoxy groups (DeLuca et al., U.S. Pat. No. 5,536,713), with 2-alkyl groups (DeLuca et al., U.S. Pat. No. 5,945,410), and with 2-alkylidene groups (DeLuca et al., U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-Hydroxy-2-methylene-19-nor-pregnacalciferol is described in U.S. Pat. No. 6,566,352 while 1α-hydroxy-2-methylene-19-nor-(20S)-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to the vitamin D receptor and relatively high cell differentiation activity, but little if any calcemic activity as compared to 1α,25-dihydroxyvitamin D₃. Their biological activities make these compounds excellent candidates for a variety of pharmaceutical uses, as set forth in the '352, '861 and '622 patents.

SUMMARY OF THE INVENTION

The invention provides 19,26,27trinor-1α,25-dihydroxyvitamin D₃ compounds such as 2α-methyl-19,26,27-trinor-(20S)-1α,25-dihydroxyvitamin D₃ ("P10"), 2β-methyl-19,26,27-trinor-(20S)-1α,25-dihydroxyvitamin D₃ ("T-74"), and 2-methylene-19,26,27-trinor-(20S)-1α,25-dihydroxyvitamin D₃ ("BM"), and related compounds, pharmaceutical formulations that include these compounds, and the use of these compounds or mixtures thereof in therapy and in the preparation of medicaments for use in treating various disease states. In particular, compounds of the invention may be useful in treating biological disorders mediated by vitamin D receptors and/or in treating disorders where a rise in serum calcium is undesirable.

Therefore, in one aspect, the invention provides a 19,26,27-trinor vitamin D₃ compound of formula 1 as shown below:

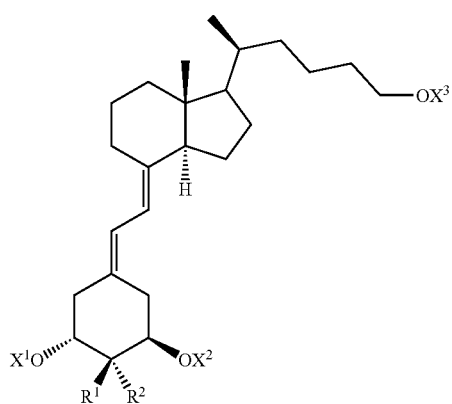

where, $X^1$, $X^2$, and $X^3$ may be the same or different and are independently selected from H or hydroxy-protecting groups;

and $R^1$ and $R^2$ are independently selected from H or straight or branched chain alkyl groups having from 1 to 8 carbon atoms; or $R^1$ and $R^2$ join together to form a group of formula 2

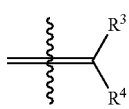

where the wavy line indicates the point of attachment to the carbon at the 2 position of the vitamin D analog and $R^3$ and $R^4$ are independently selected from H or straight or branched chain alkyl groups having from 1 to 8 carbon atoms.

In some embodiments of the compound of formula 1, $X^3$ is H.

In some embodiments of the compound of formula 1, $X^3$ is H, and the compound of formula 1 has the formula 1A as shown below where the other variables have the same values as described with respect to the compound of formula 1:

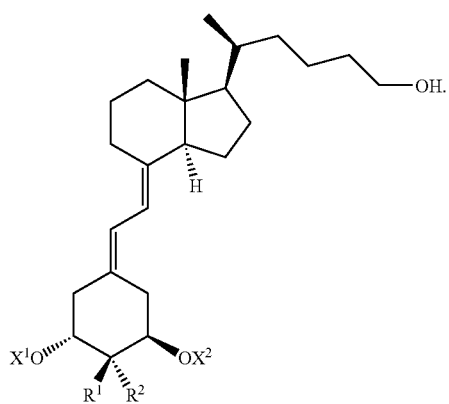

In some embodiments of the compound of formula 1A, $X^1$ and $X^2$ are both hydroxy protecting groups such as silyl groups. In some such embodiments, $X^1$ and $X^2$ are both t-butyldimethylsilyl groups. In other embodiments, $X^1$ and $X^2$ are both H.

In some embodiments of the compound of formula 1A, $R^1$ is H and $R^2$ is methyl. An example of such a compound is a compound of formula 3A as shown below which is 2β-methyl-19,26,27-trinor-(20S)-1α,25-dihydroxyvitamin $D_3$ ("T-74"):

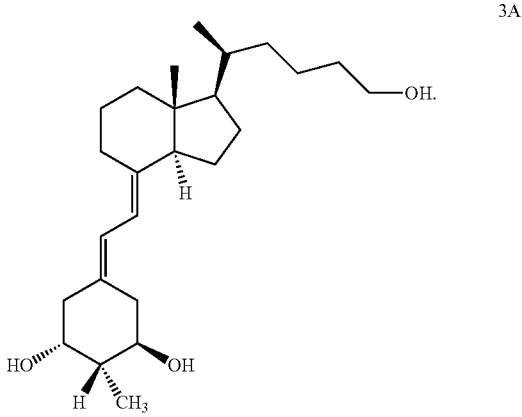

In some embodiments of the compound of formula 1A, $R^1$ is methyl and $R^2$ is H. An example of such a compound is a compound of formula 3B as shown below which is 2α-methyl-19,26,27-trinor-(20S)-1α,25-dihydroxyvitamin $D_3$ ("P10"):

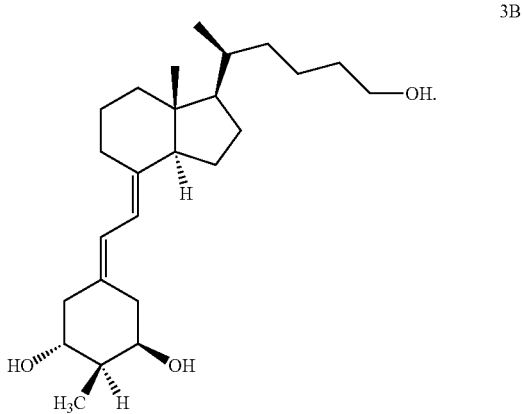

In some embodiments of the compound of formula 1A, $R^1$ and $R^2$ join together to form a group of formula 2 where $R^3$ and $R^4$ are both H. An example of such a compound is a compound of formula 3C as shown below which is 2-methylene-19,26,27-trinor-(20S)-1α,25-dihydroxyvitamin $D_3$ ("BM"):

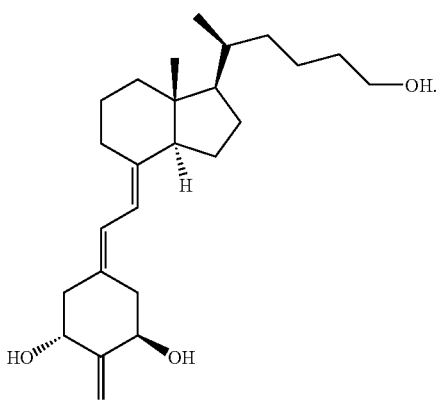

In some embodiments, the compounds of formula 3A and 3B are present in a purified form whereas in other embodiments these compounds may be present as components in a mixture that includes both compounds. In some such embodiments, the compounds are present in a purified form. In other embodiments, the compounds in a composition may be present as a mixture. In some embodiments, the mixture includes the compound of formula 3A and the compound of formula 3B, and the ratio of the compound of formula 3A to the compound of formula 3B ranges from 50:50 to 99.9:0.1. In some such embodiments, the ratio of the compound of formula 3A to the compound of formula 3B ranges from 70:30 to 99.9:0.1, from 80:20 to 99.9:0.1, from 90:10 to 99.9:0.1, or from 95:5 to 99.9:0.1. In other embodiments, the mixture includes the compound of formula 3A and the compound of formula 3B, and the ratio of the compound of formula 3B to the compound of formula 3A ranges from 50:50 to 99.9:0.1. In some such embodiments, the ratio of the compound of formula 3B to the compound of formula 3A ranges from 70:30 to 99.9:0.1, from 80:20 to 99.9:0.1, from 90:10 to 99.9:0.1, or from 95:5 to 99.9:0.1.

The above compounds exhibit desired, and highly advantageous, patterns of biological activity. P10, T-74, and BM bind to the vitamin D receptor. P10 is slightly more active in this respect than is $1\alpha,25$-dihydroxyvitamin $D_3$. BM is slightly less active in this respect than is $1\alpha,25$-dihydroxyvitamin $D_3$. T-74 binds to the vitamin D receptor, but is significantly less active than is $1\alpha,25$-dihydroxyvitamin $D_3$ in this respect. BM shows about the same activity as $1\alpha,25$-dihydroxyvitamin $D_3$ in inducing differentiation of HL-60 cells. P10 shows less activity than $1,25$-$(OH)_2D_3$ in inducing differentiation of HL-60 cells, and T-74 shows significantly less activity in inducing differentiation of HL-60 cells. P10, T-74, and BM have no calcemic activity when measured by bone calcium mobilization. They also do not elevate intestinal calcium transport. These properties suggest that these compounds will be useful in therapy, especially in treating diseases where elevation of calcium is undesirable. Such diseases include autoimmune diseases such as rheumatoid arthritis, multiple sclerosis, type I diabetes, lupus, renal osteodystrophy and secondary hyperparathyroidism.

The compounds described herein are also characterized by moderate cell differentiation activity. Thus, in some embodiments of methods of the invention, cell differentiation is induced in a subject in need thereof by administering a compound or pharmaceutical composition as described herein to the subject. It will be readily appreciated that such treatment raises the subject's level of cell differentiation beyond the level existing prior to treatment. Thus, compounds of the invention may be used as therapeutic agents for the treatment of psoriasis and/or as anti-cancer agents, especially against leukemia, colon cancer, breast cancer and prostate cancer. In addition, due to their moderate cell differentiation activities, the compounds may be used as therapeutic agents for the treatment of various skin conditions including wrinkles, lack of adequate dermal hydration, i.e. dry skin, lack of adequate skin firmness, i.e. slack skin, and insufficient sebum secretion. Use of the compounds thus moisturizes skin and improves the barrier function of skin.

In some embodiments of the methods of the invention, the compound or pharmaceutical composition is administered orally, rectally, parenterally, transdermally, or topically. In other embodiments, the compound or pharmaceutical formulations is administered in an aerosol which may be accomplished using an inhaler or a nebulizer.

The compounds of the invention may be used to prepare pharmaceutical formulations or medicaments that include a compound or a mixture of the compounds of the invention in combination with a pharmaceutically acceptable carrier. Such pharmaceutical formulations and medicaments may be used to treat various biological disorders such as those described herein, including those mediated by a vitamin D receptor. Methods for treating such disorders typically include administering an effective amount of the compound, or an appropriate amount of a pharmaceutical formulation or a medicament that includes the compound, to a subject suffering from the biological disorder. In some embodiments, the subject is a mammal. In some such embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the subject is a primate such as, in some embodiments, a human.

The compounds may be present in a composition to treat the above-noted diseases and disorders in an amount from about 0.01 μg/gm to about 1 mg/gm of the composition, preferably from about 0.1 μg/gm to about 500 μg/gm of the composition, and may be administered topically, transdermally, orally, rectally, or parenterally in dosages of from about 0.01 μg/day to about 1 mg/day, preferably from about 0.1 μg/day to about 500 μg/day.

Further objects, features and advantages of the invention will be apparent from the following detailed description and drawings.

BRIEF DESCRIPTION OF THE DRAWINGS

FIG. 1 is a graph comparing the relative activity of P10, T-74, and 1,25$(OH)_2D_3$ to compete for binding with [3H]-1,25-$(OH)_2$-$D_3$ to the full-length recombinant rat vitamin D receptor.

FIG. 2 is a graph comparing the relative activity of BM and 1,25$(OH)_2D_3$ to compete for binding with [3H]-1,25-$(OH)_2$-$D_3$ to the full-length recombinant rat vitamin D receptor.

FIG. 3 is a graph comparing the percent HL-60 cell differentiation as a function of concentration of P10, T-74, BM, and 1,25$(OH)_2D_3$.

FIG. 4 is a graph comparing the in vitro transcription activity of P10, T-74, BM, and 1,25$(OH)_2D_3$.

FIG. 5 is a bar graph comparing the bone calcium mobilization activity of P10, T-74, BM, and 1,25(OH)$_2$D$_3$.

FIG. 6 is a bar graph comparing the intestinal calcium transport activity of P10, T-74, BM, and 1,25(OH)$_2$D$_3$.

FIG. 7 is a bar graph comparing the bone calcium mobilization activity of BM and 1,25(OH)$_2$D$_3$.

FIG. 8 is a bar graph comparing the intestinal calcium transport activity of BM and 1,25(OH)$_2$D$_3$.

DETAILED DESCRIPTION OF THE INVENTION

Figure 1:
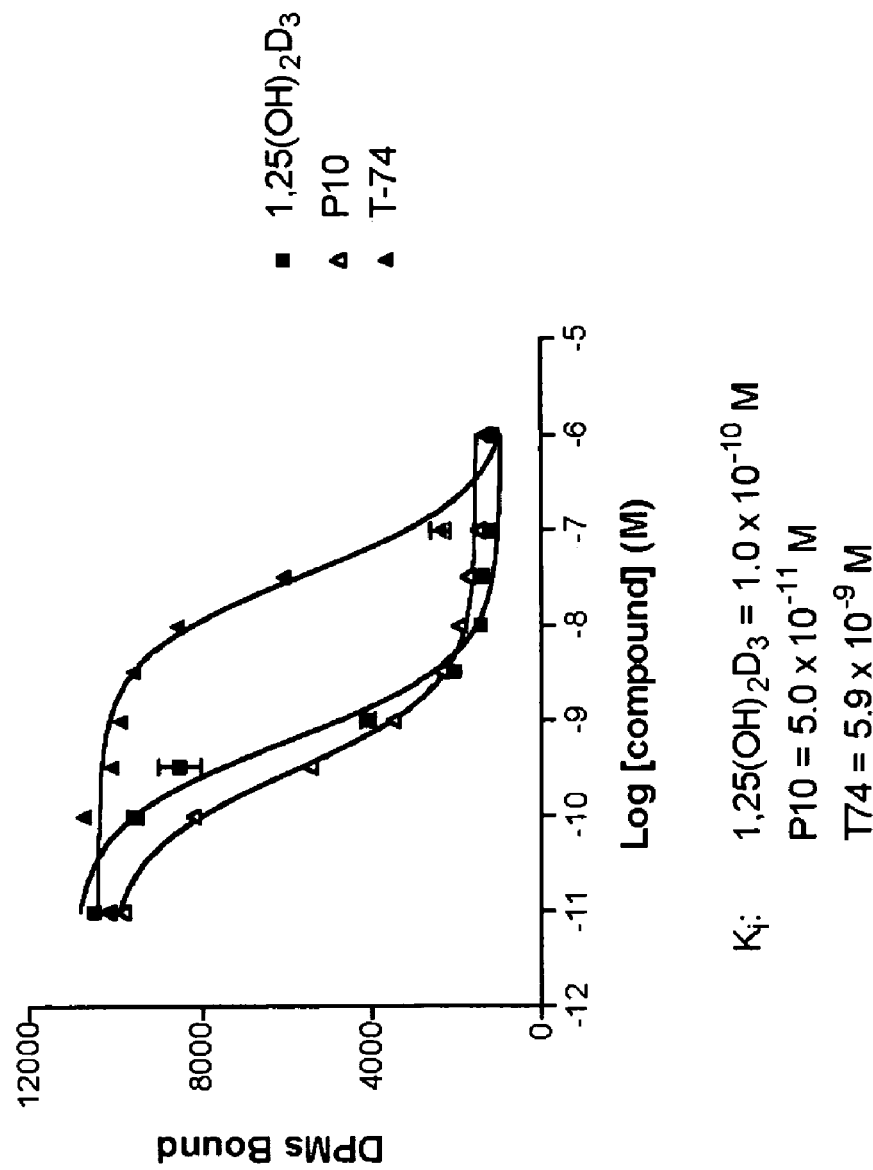
FIGS. 1-8 illustrate various biological activities of 2α-methyl-19,26,27-trinor-(20S)-1α,25-dihydroxyvitamin $D_3$ (referred to as "P10" in the Figures), 2β-methyl-19,26,27-trinor (20S)-1α,25-dihydroxyvitamin $D_3$ (referred to as "T-74" in the Figures), and 2-methylene-19,26,27-trinor-(20S)-1α,25-dihydroxyvitamin $D_3$ (referred to as "BM" in the Figures) compared with those of the native hormone, 1α,25-dihydroxyvitamin $D_3$ (referred to as "1,25$(OH)_2D_3$" in the Figures).

Various 19,26,27-trinor-1α,25-dihydroxyvitamin D$_3$ compounds such as 2α-methyl-19,26,27-trinor-(20S)-1α,25-dihydroxyvitamin D$_3$ ("P10"), 2β-methyl-19,26,27-trinor-(20S)-1α,25-dihydroxyvitamin D$_3$ ("T-74"), and 2-methylene-19,26,27-trinor-(20S)-1α,25-dihydroxyvitamin D$_3$ ("BM") were synthesized, and tested, and found to be useful in treating a variety of biological conditions as described herein.

The invention provides 19,26,27-trinor-1α,25-dihydroxyvitamin D$_3$ compounds such as 2α-methyl-19,26,27-trinor-(20S)-1α,25-dihydroxyvitamin D$_3$ ("P10"), 2α-methyl-19,26,27-trinor-(20S)-1α,25-dihydroxyvitamin D$_3$ ("T-74"), and 2-methylene-19,26,27-trinor-(20S)-1α,25-dihydroxyvitamin D$_3$ ("BM"), and related compounds, pharmaceutical formulations that include these compounds, and the use of these compounds or mixtures thereof in the preparation of medicaments for use in treating various disease states.

In one aspect, the invention provides a 19,26,27-trinor vitamin D$_3$ compound of formula 1 as shown below:

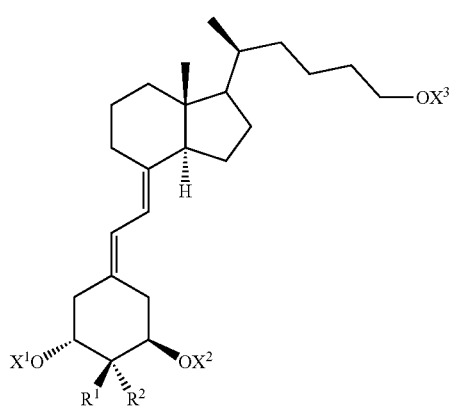

1 where, $X^1$, $X^2$, and $X^3$ may be the same or different and are independently selected from H or hydroxy-protecting groups;

and $R^1$ and $R^2$ are independently selected from H or straight or branched chain alkyl groups having from 1 to 8 carbon atoms; or $R^1$ and $R^2$ join together to form a group of formula 2

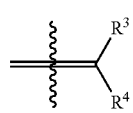

2 where the wavy line indicates the point of attachment to the carbon at the 2 position of the vitamin D analog and $R^3$ and $R^4$ are independently selected from H or straight or branched chain alkyl groups having from 1 to 8 carbon atoms. Examples of straight or branched chain alkyl groups having from 1 to 8 carbon atoms include straight chain alkyl groups such as methyl, ethyl, propyl, butyl, pentyl, hexyl, heptyl, and octyl. Examples of branched chain alkyl groups having from 1 to 8 carbon atoms include —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH(CH$_3$)CH$_2$CH(CH$_3$)$_2$, —CH(CH$_3$)CH(CH$_3$)CH(CH$_3$)$_2$, —CH$_2$CH$_2$CH$_2$C(CH$_3$)$_3$, —CH$_2$CH$_2$CH$_2$CH(CH$_3$)$_2$, —CH$_2$CH$_2$CH(CH$_3$)C(CH$_3$)$_3$, —CH$_2$CH$_2$CH(CH$_3$)CH(CH$_3$)$_2$, and the like.

In some embodiments, the compound of formula 1 includes compounds in which $X^3$ is H. In some such embodiments, the compound of formula 1 has the formula 1A as shown below where the variables have the same values as described with respect to the compound of formula 1:

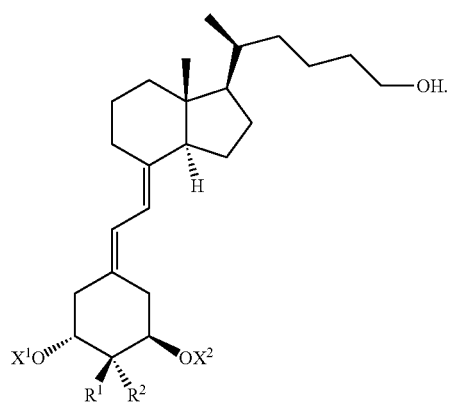

1A

In some embodiments of the compound of formula 1A, $X^1$ and $X^2$ are both hydroxy protecting groups such as silyl groups. In some such embodiments, $X^1$ and $X^2$ are both t-butyldimethylsilyl groups. In other embodiments, $X^1$ and $X^2$ are both H.

In some embodiments of the compound of formula 1A, $R^1$ is H and $R^2$ is methyl. An example of such a compound is a compound of formula 3A as shown below which is 2β-methyl-19,26,27-trinor-(20S)-1α,25-dihydroxyvitamin D$_3$ ("T-74"):

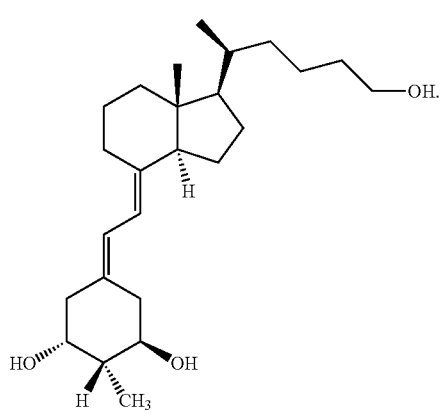

3A

In some embodiments of the compound of formula 1A, $R^1$ is methyl and $R^2$ is H. An example of such a compound is a compound of formula 3B as shown below which is 2α-methyl-19,26,27-trinor-(20S)-1α,25-dihydroxyvitamin $D_3$ ("P10"):

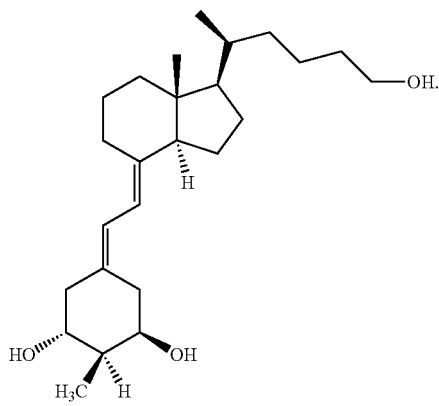

3B

In some embodiments of the compound of formula 1A, $R^1$ and $R^2$ join together to form a group of formula 2 where $R^3$ and $R^4$ are both H. An example of such a compound is a compound of formula 3C as shown below which is 2-methylene-19,26,27-trinor-(20S)-1α,25-dihydroxyvitamin $D_3$ ("BM"):

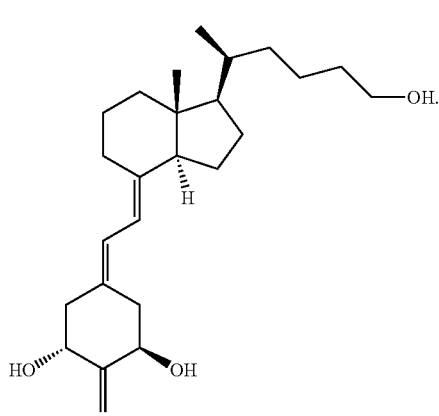

3C

One step in the reaction sequence used in the preparation of the 19,26,27-trinor-1α,25-dihydroxyvitamin $D_3$ compounds can be accomplished by condensing an appropriate bicyclic Windaus-Grundmann type ketone (II) with the allylic phosphine oxide III followed by TBS removal, and deprotection (removal of the $Y_1$ and $Y_2$ groups), in a later step.

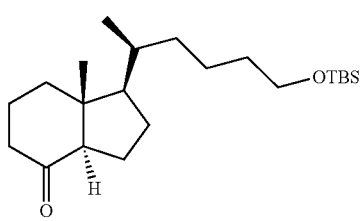

II

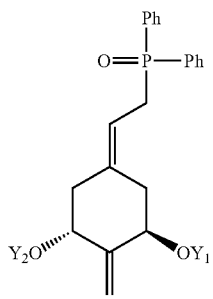

III

In phosphine oxide III, $Y_1$ and $Y_2$ are preferably hydroxy-protecting groups such as silyl protecting groups. The t-butyldimethylsilyl (TBDMS or TBS) group is an example of a particularly useful hydroxy-protecting group. The process described above represents an application of the convergent synthesis concept, which has been applied effectively to the preparation of numerous vitamin D compounds (see Lythgoe et al., *J. Chem. Soc. Perkin Trans. 1*, 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); Mascarenas et al., *J. Org. Chem.* 51, 1269 (1986); DeLuca et al., U.S. Pat. No. 5,086,191; DeLuca et al., U.S. Pat. No. 5,536,713; DeLuca et al., U.S. Pat. No. 5,843,928, and Clagett-Dame et al., U.S. Ser. No. 10/997,698, filed on Nov. 24, 2004, all of which are hereby incorporated by reference in their entirety and for all purposes as if fully set forth herein).

Phosphine oxide III is a convenient reagent that can be used to prepare a large number of 19-nor vitamin D compounds and may be prepared according to the procedures described by Sicinski et al., *J. Med. Chem.*, 41, 4662 (1998), DeLuca et al., U.S. Pat. No. 5,843,928; Perlman et al., *Tetrahedron Lett.* 32, 7663 (1991); and DeLuca et al., U.S. Pat. No. 5,086,191. Scheme I shows the general procedure for synthesizing phosphine oxide III as outlined in U.S. Pat. No. 5,843,928 which is hereby incorporated by reference in its entirety as if fully set forth herein. Modification of the method shown in Scheme I may be used to produce a large number of vitamin D analogs as will be apparent to those skilled in the art. For example, a wide variety of phosphonium compounds may be used in place of the $MePh_3P^+Br^-$ used to convert ketone B to alkene C. Examples of such compounds include $EtPh_3P^+Br^-$, $PrPh_3P^+Br^-$, and compounds generally prepared by reaction of triphenylphosphine with an alkyl halide, an alkenyl halide, a protected-hydroxyalkyl halide, and a protected hydroxyalkenyl halide. Alkenes prepared using this procedure may then be carried through to prepare a phosphine oxide in an analogous manner to that used to prepare phosphine oxide H in Scheme I. Alternatively, an alkene analogous to compound C of Scheme I may be reduced with $(Ph_3P)_3RhCl$ and $H_2$ to provide other vitamin D analogs. See U.S. Pat. No. 5,945,410 and Sicinski, R. R. et al., *J. Med. Chem.*, 41, 4662-4674 (1998) both of which are hereby incorporated by reference in their entireties and for all purposes. Therefore, the procedure for forming the phosphine oxide shown in Scheme I may be used to prepare a wide variety of vitamin D analogs in addition to the compound of the present invention.

Scheme I

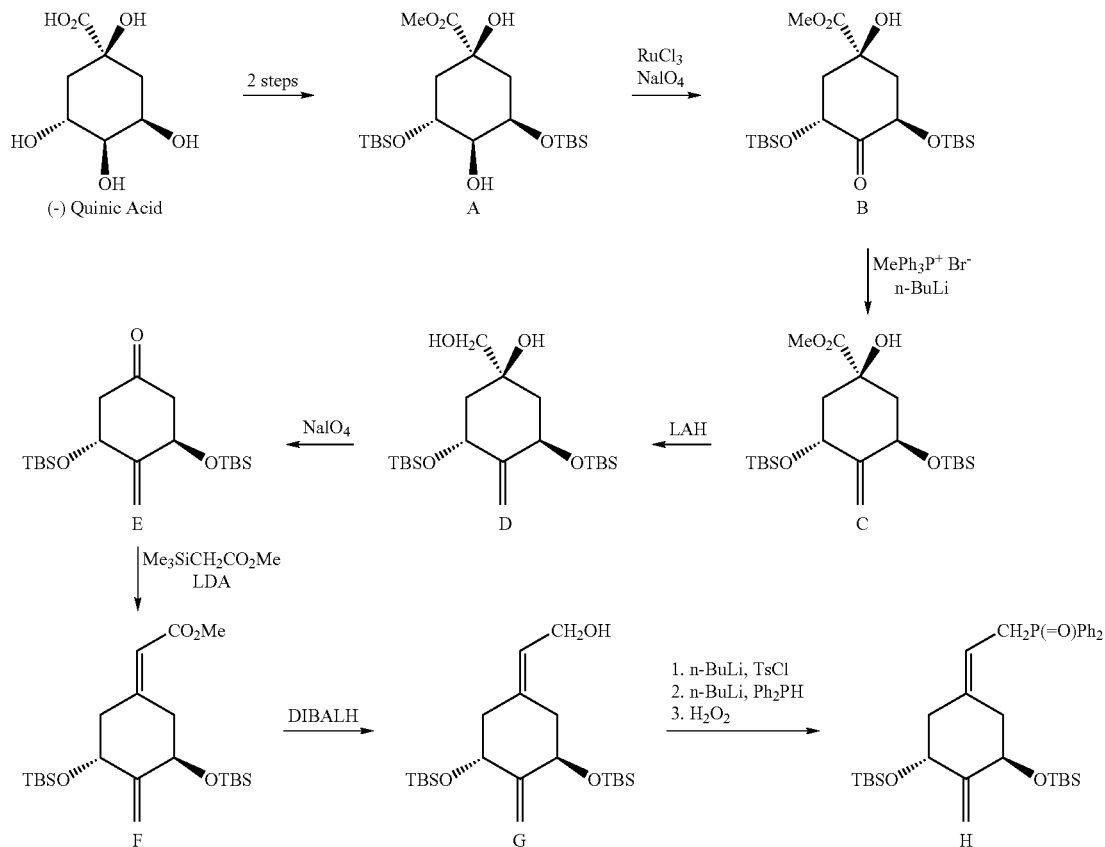

Hydroindanones of structure II can prepared by known methods or adapted methods as will be readily apparent to one of skill in the art and described herein. Specific examples of some important bicyclic ketones used to synthesize vitamin D analogs are those described in Mincione et al., *Synth. Commun* 19, 723, (1989); and Peterson et al., *J. Org. Chem.* 51, 1948, (1986).

An overall process for synthesizing 2-alkylidene-19-nor-vitamin D compounds is illustrated and described in U.S. Pat. No. 5,843,928 which is hereby incorporated by reference in its entirety and for all purposes as if fully set forth herein.

As used herein, the term "hydroxy protecting group" signifies any group commonly used for the temporary protection of the hydroxy (—OH) functional group, such as, but not limited to, alkoxycarbonyl, acyl, trialkylsilyl or dialkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groups such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for all purposes as if fully set forth herein.

A "protected hydroxy" group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

EXAMPLES

Synthesis of 2α-Methyl-19,26,27-trinor-(20S)-1α,25-dihydroxyvitamin $D_3$ ("P10"), 2β-Methyl-19,26,27-trinor-(20S)-1α,25-dihydroxyvitamin $D_3$ ("T-74"), and 2-Methylene-19,26,27-trinor-(20S)-1α,25-dihydroxyvitamin $D_3$ ("BM")

The synthesis and characteristics of various 19-nor vitamin D analogs is described in numerous United States patents including U.S. Pat. No. 5,843,928, U.S. Pat. No. 6,627,622, U.S. Pat. No. 6,579,861, U.S. Pat. No. 5,086,191, U.S. Pat. No. 5,585,369, and U.S. Pat. No. 6,537,981. Each of the above-described references is hereby incorporated by reference in its entirety and for all purposes as if fully set forth herein.

Schemes I, IIA, IIB, and IIC outline the synthetic procedures described below, in detail.

(20S)-de-A,B-8β-(tert-butyldimethylsilyl)oxy-20-(hydroxymethyl)-pregnane (2)

Ozone was passed through a solution of vitamin $D_2$ (3 g, 7.6 mmol) in methanol (250 mL) and pyridine (2.44 g, 2.5 mL, 31 mmol) for 50 minutes at −78° C. The reaction mixture was then flushed with oxygen for 15 minutes to remove the residual ozone, and the solution was treated with $NaBH_4$ (0.75 g, 20 mmol). After 20 minutes, the second portion of $NaBH_4$ (0.75 g, 20 mmol) was added and the mixture was allowed to warm to room temperature. The third portion of $NaBH_4$ (0.75 g, 20 mmol) was then added, and the reaction mixture was stirred for 18 hours. The reaction was quenched with water (40 mL), and the solution was concentrated under reduced pressure. The residue was extracted with ethyl acetate (3×80 mL) and the combined organic phase was washed with 1 M aq. HCl, saturated aq. $NaHCO_3$, dried ($Na_2SO_4$), and concentrated under reduced pressure. The residue was chromatographed on silica gel with hexane/ethyl acetate (75:25) to give (20S)-de-A,B-20-(hydroxymethyl)pregnan-8β-ol 1 (1.21 g, 75% yield) as white crystals.

tert-Butyldimethylsilyl trifluoromethanesulfonate (3.24 mL, 3.72 g, 14.1 mmol) was added to a solution of the 8β,20-diol 1 (1 g, 4.7 mmol) and 2,6-lutidine (1.64 mL, 1.51 g, 14.1 mmol) in anhydrous DMF (15 mL) at 0° C. The mixture was stirred under argon at 0° C. for 1 hour and then at room temperature for 18 hours. The reaction was quenched with water (50 mL) and extracted with ethyl acetate (3×30 mL). The combined organic phase was washed with brine, dried ($Na_2SO_4$) and concentrated under reduced pressure. The residue was dissolved in anhydrous THF (8 mL), triethylamine (3 mL, 2.17 g, 21.5 mmol) and a solution of tetrabutylammonium fluoride (1 M in THF, 6.5 mL, 6.5 mmol) was added, followed by freshly activated molecular sieves 4A (3 g). The reaction mixture was stirred under argon at room temperature for 4 hours and then filtered through a short layer of Celite and evaporated. The residue was dissolved in ethyl acetate (30 mL), washed with brine, water, dried ($Na_2SO_4$) and concentrated under reduced pressure. The pure alcohol 2 (1.42 g, 93% yield) was isolated using chromatography on silica gel with hexane/ethyl acetate (97.5:2.5 to 95:5), as a colorless oil: $[\alpha]_D$ +38.8° (c 0.83, $CHCl_3$); $^1H$ NMR (500 MHz, $CDCl_3$) δ 4.00 (1H, d, J=2.4 Hz, 8α-H), 3.63 (1H, dd, J=10.5, 3.2 Hz, 22-H), 3.39 (1H, dd, J=10.5, 6.8 Hz, 22-H), 1.94 (1H, br.d, J=12.5 Hz), 1.02 (3H, d, J=6.6 Hz, 21-$H_3$), 0.924 (3H, s, 18-$H_3$), 0.882 (9H, s, Si-t-Bu), 0.005 and −0.010 (each 3H, each s, each Si-Me); $^{13}C$ NMR (125 MHz) δ 69.29 (d, C-8), 67.94 (t, C-22), 53.06 (d), 52.80 (d), 42.12 (s, C-13), 40.54 (t), 38.27 (d), 34.39 (t), 26.79 (t), 25.79 (q, SiC$\underline{Me}_3$), 23.08 (t), 18.00 (s, Si$\underline{C}Me_3$), 17.61 (t), 16.65 (q, C-21), 13.75 (q, C-18), −4.81 and −5.18 (each q, each SiMe); MS (EI) m/z 326 (2, $M^+$), 283 (3, $M^+$—$C_3H_7$), 269 (21, $M^+$—$C_4H_9$), 251 (21, $M^+$—$C_4H_9$—$H_2O$), 193 (18, $M^+$-t-Bu$Me_2$SiOH—H), 177 (72), 135 (43), 121 (31), 107 (31), 95 (52), 75 (100); exact mass calculated for $C_{15}H_{29}O_2Si$ ($M^+$—$C_4H_9$) 269.1937, found 269.1932.

(20S)-de-A,B-8β-(tert-butyldimethylsilyl)oxy-20-formylpregnane (3)

Sulfur trioxide pyridine complex (1.32 g, 8.28 mmol) was added to a solution of the alcohol 2 (451 mg, 1.38 mmol), triethylamine (960 μL, 697 mg, 6.9 mmol) in anhydrous methylene chloride (20 mL), and anhydrous DMSO (5 mL) at 0° C. The reaction mixture was stirred under argon at 0° C. for 20 minutes and then concentrated. The residue was purified by column chromatography on silica gel with hexane/ethyl acetate (95:5) to give the aldehyde 3 (364 mg, 81% yield) as an oil: $[\alpha]_D$ +43.80° (c 1.31, $CHCl_3$); $^1H$ NMR (500 MHz, $CDCl_3$) δ 9.55 (1H, d, J=3.1 Hz, CHO), 4.00 (1H, s, 8α-H), 2.33 (1H, m, 20-H), 1.89 (1H, dm, J=12.4 Hz), 1.07 (3H, d, J=6.8 Hz, 21-$H_3$), 0.939 (3H, s, 18-$H_3$), 0.862 (9H, s, Si-t-Bu), −0.009 and −0.026 (each 3H, each s, each SiMe); $^{13}C$ NMR (125 MHz) δ 205.37 (d, CHO), 68.99 (d, C-8), 52.28 (d), 51.58 (d), 49.15 (d), 42.58 (s, C-13), 40.35 (t), 34.29 (t), 26.16 (t), 25.74 (q, SiC$\underline{Me}_3$), 23.27 (t), 17.96 (s, Si$\underline{C}Me_3$), 17.52 (t), 14.04 (q, C-21), 13.28 (q, C-18), −4.85 and −5.23 (each q, each Si$\underline{Me}$); MS (EI) m/z 324 (4, $M^+$), 309 (3, $M^+$—$CH_3$), 281 (8, $M^+$—$C_3H_7$), 267 (48, $M^+$—$C_4H_9$), 209 (6, $M^+$-t-Bu$Me_2$Si), 191 (16, $M^+$-t-Bu$Me_2$SiOH—H), 175 (95), 135 (68), 119 (33), 93 (33), 75 (100); exact mass calculated for $C_{19}H_{36}O_2Si$ ($M^+$) 324.2485, found 324.483.

(20R)-de-A,B-8β-(tert-butyldimethylsilyl)oxy-20-(hydroxymethyl)pregnane (4)

The aldehyde 3 (364 mg, 1.12 mmol) was dissolved in methylene chloride (15 mL) and a 40% aqueous n-$Bu_4$NOH solution (1.47 mL, 1.45 g, 2.24 mmol) was added. The resulting mixture was stirred under argon at room temperature for 16 hours, diluted with methylene chloride (20 mL), washed with water, dried ($Na_2SO_4$), and concentrated under reduced pressure. The residue was chromatographed on silica gel with hexane/ethyl acetate (95:5) to afford a mixture of aldehyde 3 and its 20-epimer (292 mg, 80% yield) in ca. 1:2 ratio (by $^1H$ NMR).

This mixture of aldehydes (292 mg, 0.9 mmol) was dissolved in THF (5 mL) and $NaBH_4$ (64 mg, 1.7 mmol) was added, followed by a dropwise addition of ethanol (5 mL). The reaction mixture was stirred at room temperature for 30 minutes and then quenched with a saturated aqueous $NH_4Cl$ solution. The mixture was extracted with ether (3×20 mL) and the combined organic phase was washed with water, dried ($Na_2SO_4$), and concentrated under reduced pressure. The residue was chromatographed on silica gel with hexane/ethyl acetate (96:4 to 80:20) to give the desired, pure (20R)-alcohol 4 (160 mg, 55% yield) as an oil and a mixture of 4 and its 20-epimer 2 (126 mg, 43% yield) in about a 1:3 ratio (as determined by $^1H$ NMR). 4: $[\alpha]_D$ +40.8° (c 1.09, $CHCl_3$); $^1H$ NMR (500 MHz, $CDCl_3$) δ 4.00 (1H, d, J=1.9 Hz, 8α-H), 3.70 (1H, dd, J=10.6, 3.2 Hz, 22-H), 3.43 (1H, dd, J=10.6, 7.0 Hz, 22-H), 0.94 (3H, d, J=6.7 Hz, 21-$H_3$), 0.927 (3H, s, 18-$H_3$), 0.884 (9H, s, Si-t-Bu), 0.007 and −0.006 (each 3H, each s, Si$Me_2$); $^{13}C$ NMR (125 MHz) δ 69.30 (d, C-8), 66.83 (t, C-22), 53.02 (d), 52.96 (d), 41.91 (s, C-13), 40.12 (t), 37.48 (d), 34.38 (t), 26.71 (t), 25.79 (q, SiC$\underline{Me}_3$), 22.85 (t), 18.01 (s, Si$\underline{C}Me_3$), 17.64 (t), 16.58 (q, C-21), 14.07 (q, C-18), −4.81 and −5.18 (each q, each Si $\underline{Me}$); MS (EI) m/z 326 (3, $M^+$), 311 (3, $M^+$—$CH_3$), 283 (4, $M^+$—$C_3H_7$), 269 (62, $M^+$—$C_4H_9$), 251 (100, $M^+$—$C_4H_9$—$H_2O$), 193 (35, $M^+$-t-Bu$Me_2$SiOH—H), 177 (29), 135 (56), 121 (28), 107 (24), 95 (41), 75 (99); exact mass calculated for $C_{19}H_{38}O_2Si$ ($M^+$) 326.2641, found 326.2635.

(20R)-de-A,B-8β-(tert-butyldimethylsilyl)oxy-20-(iodomethyl)pregnane (5)

A solution of iodine (471 mg, 1.84 mmol) in methylene chloride (30 mL) was slowly added to a solution of triphenylphosphine (482 mg, 1.84 mmol) and imidazole (250 mg, 3.68 mmol) in methylene chloride (15 mL) at 0° C. After 15 minutes, a solution of alcohol 4 (149 mg, 0.46 mmol) in methylene chloride (3 mL) was added into the mixture. After being stirring for 20 minutes at 0° C., followed by 18 hours at room temperature, the reaction mixture was washed with water, dried ($Na_2SO_4$), and concentrated under reduced pressure. The residue was chromatographed on silica gel with hexane/ethyl acetate (97:3) to give the desired iodide 5 (201 mg, 100%): $[\alpha]_D$ –0.3° (c 0.97, $CHCl_3$); $^1H$ NMR (500 MHz, $CDCl_3$) δ 3.99 (1H, s, 8α-H), 3.46 (1H, dd, J=9.5, 2.9 Hz, 22-H), 3.18 (1H, dd, J=9.5, 6.4 Hz), 1.88-1.74 (3H, m), 1.67 (1H, dm, J=13.9 Hz), 0.95 (3H, d, J=6.4 Hz, 21-$H_3$), 0.918 (3H, s, 18-$H_3$), 0.882 (9H, s, Si-t-Bu 0.008 and –0.008 (each, 3H, each s, $SiMe_2$); $^{13}C$ NMR (125 MHz) δ 69.27 (d, C-8), 55.19 (d), 52.69 (d), 41.99 (s, C-13), 40.48 (t), 36.15 (d), 34.24 (t), 26.90 (t), 25.80 (q, $SiMe_3$), 22.81 (t), 21.38 (q, C-21), 19.58 (t), 18.02 (s, $SiCMe_3$), 17.63 (t), 14.12 (q, C-18), –4.79 and –5.17 (each q, each SiMe); MS (EI) m/z 436 (15, M$^+$), 421 (8, M$^+$—$CH_3$), 393 (9, M$^+$—$C_3H_7$), 379 (98, M$^+$-t-Bu), 303 (65, M$^+$-t-Bu$Me_2$SiOH—H), 177 (70), 135 (70), 95 (55), 75 (100); exact mass calculated for $C_{19}H_{37}OSiI$ (M$^+$) 436.1658, found 436.1672.

(20S)-de-A,B-8β-(tert-butyldimethylsilyl)oxy-20-(3-isopropoxycarbonyl)propyl-pregnane (6)

A mixture of zinc powder (124 mg, 1.9 mmol), anhydrous pyridine (4 mL) and isopropyl acrylate (235 μL, 217 mg, 1.9 mmol) was warmed to 50° C., then nickel(II) chloride hexahydrate (109 mg, 0.46 mmol) was added. The resulting mixture was warmed to 65° C. and stirred for 2 hours until the green color turned to reddish brown. After cooling to 0° C., a solution of iodide 5 (222 mg, 0.51 mmol) in anhydrous pyridine (3 mL) was added, and the reaction mixture was stirred for 4 hours at room temperature. The mixture was diluted with ethyl acetate (20 mL), and the resulting precipitate was filtered off through a pad of Celite. The filtrate was washed with 5% aqueous HCl and brine, dried ($Na_2SO_4$) and concentrated under reduced pressure. The residue was chromatographed on silica gel with hexane and hexane/ethyl acetate (95:5) to give the ester 6 (177 mg, 82%): $[\alpha]_D$ +19.7° (c 1.13, $CHCl_3$); $^1H$ NMR (400 MHz, $CDCl_3$) δ 5.00 (1H, sep, J=6.3 Hz, OC$H$Me$_2$), 3.99 (1H, d, J=2.2 Hz, 8α-H), 2.22 (2H, dt, J=7.1, 2.2 Hz, 24-$H_2$), 1.90 (1H, dm, J=12.2 Hz), 1.22 (6H, d, J=6.3 Hz, OCH$ME_2$), 0.895 (3H, s, 18-$H_3$), 0.881 (9H, s, Si-t-Bu, 0.82 (3H, d, J=6.6 Hz, 21-$H_3$), 0.001 and –0.012 (each, 3H, each s, $SiMe_2$); $^{13}C$ NMR (100 MHz) δ 173.48 (s, $C$OO-iPr), 69.45 (d, C-8), 67.31 (d, COO$C$HMe$_2$), 56.29 (d), 53.08 (d), 42.16 (s, C-13), 40.64 (t), 35.05 (t), 34.71 (t), 34.51 (d), 34.44 (t), 27.16 (t), 25.80 (q, SiC$Me_3$), 22.93 (t), 21.92 (t), 21.86 (q, COOCH$Me_2$), 18.48 (q, C-21), 18.02 (t), 17.69 (s, Si$C$Me$_3$), 14.01 (q, C-18), –4.79 and –5.16 (each q, each Si$Me$); MS (EI) m/z 424 (5, M$^+$), 409 (15, M$^+$—$CH_3$), 381 (35, M$^+$—$C_3H_7$), 367 (89, M$^+$-t-Bu), 321 (39, M$^+$—$CH_3COOCHMe_2$-H), 307 (85, M$^+$—$CH_3CH_2COOCHMe_2$-H), 283 (65), 265 (41), 249 (45), 233 (60), 215 (73), 189 (70), 163 (78), 135 (86), 109 (70), 95 (79), 75 (100); exact mass calculated for $C_{25}H_{48}O_3Si$ (M$^+$) 424.3373, found 424.3371.

(20S)-de-A,B-20-(3-isopropoxycarbonyl)propyl-pregnan-8β-ol (7)

To a solution of compound 6 (94 mg, 0.22 mmol) in acetonitrile (3 mL), was added a mixture of aqueous 48% HF/acetonitrile (1:9 ratio, 2 mL) at 0° C. and the resulting mixture was stirred at room temperature for 2 days. Saturated aqueous $NaHCO_3$ solution was added, and the reaction mixture was extracted with ethyl acetate. The combined organic phase was washed with brine, dried ($Na_2SO_4$) and concentrated under reduced pressure. The residue was chromatographed on silica gel with hexane/ethyl acetate (97:3, 95:5) to give the recovered substrate 6 (9 mg, 0.02 mmol) and the desired product 7 (51 mg, 80%): $[\alpha]_D$ +10.1° (c 2.5, $CHCl_3$); $^1H$ NMR (400 MHz, $CDCl_3$) δ 4.99 (1H, sep, J=6.3 Hz, OC$H$Me$_2$), 4.06 (1H, d, J=2.2 Hz, 8α-H), 2.22 (2H, dt, J=7.4, 1.6 Hz, 24-$H_2$), 1.93 (1H, dm, J=11.9 Hz), 1.22 (6H, d, J=6.3 Hz, OCH$Me_2$), 0.913 (3H, s, 18-$H_3$), 0.86 (3H, d, J=6.6 Hz, 21-$H_3$); $^{13}C$ NMR (100 MHz) δ 173.42 (s, $C$OO-iPr), 69.35 (d, C-8), 67.33 (d, COO$C$HMe$_2$), 56.16 (d), 52.62 (d), 41.87 (s, C-13), 40.30 (t), 34.98 (t), 34.61 (t), 34.51 (d), 33.55 (t), 27.02 (t), 22.37 (t), 21.90 (t), 21.84 (q, COOCH$Me_2$), 18.41 (q, C-21), 17.44 (t), 13.77 (q, C-18); MS (EI) m/z 310 (48, M$^+$), 292 (76, M$^+$—$H_2O$), 277 (22, M$^+$—$H_2O$—$CH_3$), 250 (87, M$^+$—$H_2O$—$C_3H_6$), 233 (66, M$^+$—$H_2O$—$C_3H_7O$), 222 (24, M$^+$—$Me_2CHCOOH$), 196 (40), 163 (72), 154 (74), 135 (92), 125 (90), 112 (94), 97 (98), 81 (100); exact mass calculated for $C_{19}H_{34}O_3$ (M$^+$) 310.2508, found 310.2508.

(20S)-de-A,B-20-(4-hydroxybutyl)-pregnan-8β-ol (8)

Lithium aluminum hydride (40 mg, 1.05 mmol) was added to a solution of ester 7 (55 mg, 0.18 mmol) in anhydrous THF (8 mL) at 0° C. The cooling bath was removed, and the reaction mixture was stirred for 30 minutes at room temperature. The excess hydride was quenched by careful, successive addition of saturated aqueous $NH_4Cl$. A saturated aqueous solution of tartaric acid was added, and the mixture was extracted with methylene chloride. The combined organic phase was washed with water, dried ($Na_2SO_4$) and concentrated under reduced pressure. The residue was chromatographed on silica gel with hexane/ethyl acetate (95:5, 9:1, 8:2) to give the diol 8 (44 mg, 96%): $[\alpha]_D$ +12.6° (c 2.2, $CHCl_3$); $^1H$ NMR (500 MHz, $CDCl_3$+TMS) δ 4.07 (1H, s, 8α-H), 3.63 (2H, t, J=6.6 Hz, 25-$H_2$), 1.97 (1H, dm, J=12.7 Hz), 0.927 (3H, s, 18-$H_3$), 0.82 (3H, d, J=6.6 Hz, 21-$H_3$); $^{13}C$ NMR (125 MHz) δ 69.29 (d, C-8), 62.96 (t, C-25), 56.13 (d), 52.58 (d), 41.82 (s, C-13), 40.27 (t), 34.96 (t), 34.66 (d), 33.48 (t), 33.10 (t), 26.99 (t), 22.34 (t), 22.33 (t), 18.43 (q, C-21), 17.43 (t), 13.73 (q, C-18); MS (EI) m/z 254 (37, M$^+$), 236 (35, M$^+$—$H_2O$), 221 (28, M$^+$—$H_2O$—$CH_3$), 163 (32), 157 (33), 135 (78), 125 (81), 111 (97), 97 (95), 81 (100); exact mass calculated for $C_{16}H_{30}O$ (M$^+$) 254.2246, found 254.2454.

(20S)-de-A,B-20-[4-(tert-butyldimethylsilyloxy)butyl]-pregnan-8β-ol (9)

tert-Butyldimethylsilyl chloride (18 mg, 0.12 mmol) was added to a solution of the diol 8 (23 mg, 0.09 mmol) and 2,6-lutidine (42 μL, 39 mg, 0.36 mmol) in anhydrous methylene chloride (2 mL). The mixture was stirred under argon at room temperature for 18 hours. The reaction was quenched with water and extracted with ethyl acetate. The combined organic phase was washed with brine, dried ($Na_2SO_4$) and concentrated under reduced pressure. The residue was chromatographed on silica gel with hexane and hexane/ethyl acetate (98:2) to give the alcohol 9 (31 mg, 94%): $[\alpha]_D$ +7.7° (c 1.6, CHCl$_3$); $^1$H NMR (400 MHz, CDCl$_3$+TMS) δ 4.07 (1H, d, J=2.0 Hz, 8α-H), 3.60 (2H, t, J=6.5 Hz, 25-H$_2$), 1.97 (1H, dm, J=13.1 Hz), 0.928 (3H, s, 18-H$_3$), 0.895 (9H, s, Si-t-Bu), 0.82 (3H, d, J=6.6 Hz, 21-H$_3$), 0.047 (6H, s, SiMe$_2$); $^{13}$C NMR (100 MHz) δ 69.43 (d, C-8), 63.31 (t, C-25), 56.23 (d), 52.67 (d), 41.89 (s, C-13), 40.32 (t), 35.02 (t), 34.74 (d), 33.60 (t), 33.25 (t), 27.05 (t), 25.97 (q, SiC$\underline{Me}_3$), 22.42 (t), 22.36 (t), 18.50 (q, C-21), 18.36 (s, Si$\underline{C}$Me$_3$), 17.47 (t), 13.78 (q, C-18), −5.24 (q, Si$\underline{Me}_2$); MS (EI) m/z 369 (0.5, M$^+$+H), 352 (1, M$^+$—CH$_4$), 311 (2, M$^+$—C$_4$H$_9$), 295 (10, M$^+$—C$_4$H$_9$—CH$_4$), 219 (39, M$^+$—H$_2$O-t-BuSiMe$_2$O), 163 (60), 135 (54), 123 (66), 109 (100), 95 (69), 83 (78); exact mass calculated for C$_{22}$H$_{45}$O$_2$Si (M$^+$+H) 369.3189, found 369.3177.

(20S)-de-A,B-20-[4-(tert-butyldimethylsilyloxy)-butyl]-pregnan-8-one (10)

Pyridinium dichromate (123 mg, 0.33 μmol) was added to a solution of the alcohol 9 (30 mg, 82 μmol) and pyridinium p-toluenesulfonate (3 mg, 12 μmol) in anhydrous methylene chloride (6 mL). The resulting suspension was stirred at room temperature for 3 hours. The reaction mixture was filtered through a Waters silica Sep-Pak cartridge (5 g) and was further washed with methylene chloride. After removal of solvents, the ketone 10 (27 mg, 90% yield) was obtained as a colorless oil: $[\alpha]_D$ −27.4° (c 1.5, CHCl$_3$); $^1$H NMR (400 MHz, CDCl$_3$+TMS) δ 3.61 (2H, t, J=6.4 Hz, 25-H$_2$), 2.44 (1H, dd, J=11.5, 7.7 Hz), 0.899 (9H, s, Si-t-Bu), 0.85 (3H, d, J=5.9 Hz, 21-H$_3$), 0.635 (3H, s, 18-H$_3$), 0.052 (6H, s, SiMe$_2$); $^{13}$C NMR (100 MHz) δ 212.03 (s, C-8), 63.19 (t, C-25), 62.00 (d), 56.16 (d), 49.92 (s, C-13), 40.95 (t), 38.85 (t), 35.25 (t), 34.84 (d), 33.18 (t), 27.13 (t), 25.95 (q, SiC$\underline{Me}_3$), 24.03 (t), 22.33 (t), 18.93 (t), 18.44 (q, C-21), 18.33 (s, Si$\underline{C}$Me$_3$), 12.71 (q, C-18), −5.28 (q, Si$\underline{Me}_2$); MS (EI) m/z no M$^+$, 351 (2, M$^+$—CH$_3$), 323 (3, M$^+$—C$_3$H$_7$), 309 (62, M$^+$—C$_4$C$_9$), 217 (24, M$^+$—H$_2$O-t-BuSiMe$_2$O), 161 (23), 135 (100), 121 (33), 109 (32), 95 (35), 75 (83); exact mass calculated for C$_{18}$H$_{33}$O$_2$Si (M$^+$—C$_4$H$_9$) 309.2250, found 309.2257.

(20S)-2-methylene-19,26,27-trinor-1α,25-dihydroxycalciferol (13)

To a solution of phosphine oxide 11 (102 mg, 175 μmol) in anhydrous THF (700 μL) at −20° C. was slowly added PhLi (1.3 M in cyclohexane-ether, 225 μL, 293 μmol) under argon with stirring. The solution turned deep orange. After 30 minutes the mixture was cooled to −78° C. and a precooled (−78° C.) solution of ketone 10 (27 mg, 74 μmol) in anhydrous THF (300 μL) was slowly added. The mixture was stirred under argon at −78° C. for 3 hours and at 0° C. for 18 hours. Ethyl acetate was added, and the organic phase was washed with brine, dried (Na$_2$SO$_4$) and evaporated. The residue was dissolved in hexane and applied on a Waters silica Sep-Pak cartridge (2 g). The cartridge was washed with hexane and hexane/ethyl acetate (99.5:0.5) to give 19-norvitamin derivative 12 (49 mg). The Sep-Pak was then washed with hexane/ethyl acetate (96:4) to recover the unchanged C,D-ring ketone 10 (4 mg, 11 μmol), and with ethyl acetate to recover diphenylphosphine oxide 11 (68 mg). The protected vitamin 12 was further purified by HPLC (10×250 mm Zorbax-Silica column, 4 mL/min) using a hexane/2-propanol (99.9:0.1) solvent system. Pure compound 12 (43 mg, 93% yield) was eluted at R$_t$=4.07 minutes as a colorless oil: UV (in hexane) λ$_{max}$ 262.3, 252.0, 243.6 nm; $^1$H NMR (500 MHz, CDCl$_3$) δ 6.23 and 5.83 (each 1H, each d, J=11.2 Hz, 6- and 7-H), 4.97 and 4.92 (each 1H, each s, =CH$_2$), 4.41 (2H, m, 1β- and 3α-H), 3.60 (2H, t, J=6.5 Hz, 25-H$_2$), 2.82 (1H, dm, J=12.4 Hz, 9β-H), 2.55 (1H, dd, J=13.3, 5.9 Hz, 10α-H), 2.47 (1H, dd, J=12.6, 4.4 Hz, 4α-H), 2.33 (1H, dd, J=13.3, 2.6 Hz, 10β-H), 2.18 (1H, dd, J=12.6, 8.3 Hz, 4β-H), 1.98 (2H, m), 1.86 (1H, m), 0.890 (18H, s, 2×Si-t-Bu), 0.849 (9H, s, Si-t-Bu), 0.82 (3H, d, J=6.5 Hz, 21-H$_3$), 0.524 (3H, s, 18-H$_3$), 0.077 (3H, s, SiMe), 0.059 (3H, s, SiMe), 0.051(9H, s, 3×SiMe), 0.015 (3H, s, SiMe); $^{13}$C NMR (100 MHz) δ 152.98 (s, C-2), 141.22 (s, C-8), 132.71 (s, C-5), 122.42 (d, C-6), 116.10 (d, C-7), 106.26 (t, =CH$_2$), 72.52 and 71.63(each d, C-1 and C-3), 63.32 (t), 56.32 (d), 56.16 (d), 47.61 (t), 45.70 (s, C-13), 40.51 (t), 38.55 (t), 35.50 (d), 35.30 (t), 33.24 (t), 28.76 (t), 27.41 (t), 25.99 (q, SiC$\underline{Me}_3$), 25.84 (q, SiC$\underline{Me}_3$), 25.78 (q, SiC$\underline{Me}_3$), 23.43 (t), 22.42 (t), 22.10 (t), 18.56 (q, C-21), 18.37 (s, Si$\underline{C}$Me$_3$), 18.25 (s, Si$\underline{C}$Me$_3$), 18.16 (s, Si$\underline{C}$Me$_3$), 12.31 (q, C-18), −4.87 and −5.10 and −5.25 (each q, 6×Si$\underline{Me}$); MS (EI) m/z no M$^+$, 673 (11, M$^+$—C$_4$H$_9$), 628 (3, M$^+$-t-BuMeSiH$_2$), 612 (3, M$^+$-t-BuMeSiH$_2$—CH$_4$), 598 (100, M$^+$-t-BuMe$_2$SiOH), 584 (4), 541 (6), 496 (3), 366 (45), 257 (12), 234 (12), 147 (21), 73 (84); exact mass calculated for C$_{39}$H$_{73}$O$_3$Si$_3$ (M$^+$—C$_4$H$_9$) 673.4868, found 673.4859.

Protected vitamin 12 (19 mg, 26 μmol) was dissolved in THF (2 mL) and acetonitrile (2 mL). A solution of aqueous 48% HF in acetonitrile (1:9 ratio, 1 mL) was added at 0° C., and the resulting mixture was stirred at room temperature for 3 hours. A saturated aqueous NaHCO$_3$ solution was added, and the reaction mixture was extracted with ethyl acetate. The combined organic phase was washed with brine, dried (Na$_2$SO$_4$) and concentrated under reduced pressure. The residue was diluted with 2 mL of hexane/ethyl acetate (8:2) and applied on a Waters silica Sep-Pak cartridge (2 g). Elution with hexane/ethyl acetate (8:2) and ethyl acetate gave the crude product 13 (15 mg). The vitamin 13 was further purified by straight phase HPLC [10×250 mm Zorbax-Silica column, 4 mL/min, hexane/2-propanol (85:15) solvent system, R$_t$=7.77 min.] and later by reverse phase HPLC [9.4×250 mm Zorbax Eclipse XDB-C18 column, 3 ml/min, methanol/water (85:15) solvent system, R$_t$=9.97 min.] to give a colorless oil (8.8 mg, 87% yield): UV (in EtOH) λ$_{max}$ 261.1, 251.0, 243.0 nm; $^1$H NMR (500 MHz, CDCl$_3$) δ 6.34 and 5.87 (1H and 1H, each d, J=11.2 Hz, 6- and 7-H), 5.09 and 5.07 (each 1H, each s, =CH$_2$), 4.46 (2H, m, 1β- and 3α-H), 3.63 (2H, t, J=6.5 Hz, 25-H$_2$), 2.87 (1H, dd, J=12.8, 3.8 Hz, 10β-H), 2.80 (1H, br d, J=13.3 Hz, 9β-H), 2.54 (1H, br d, J=13.3 Hz, 4α-H), 2.33 (1H, dd, J=13.3, 5.8 Hz, 4β-H), 2.25 (1H, dd, J=12.8, 8.7 Hz, 10α-H), 0.82 (3H, d, J=6.4 Hz, 21-H$_3$), 0.521 (3H, s, 18-H$_3$); $^{13}$C NMR (125 MHz) δ 151.68 (s, C-2), 143.43 (s, C-8), 130.40 (s, C-5), 124.06 (d, C-6), 115.15 (d, C-7), 107.80 (t, =CH$_2$), 71.74 and 70.38 (each d, C-1 and C-3), 63.09 (t, C-25), 56.20 (d), 55.83 (d), 45.68 (s, C-13), 45.46 (t), 40.17 (t), 37.93 (t), 35.48 (d), 35.04 (t), 33.02 (t), 28.82 (t), 27.43 (t), 23.41 (t), 22.20 (t), 22.06 (t), 18.55 (q, C-21), 12.25 (q, C-18); MS (EI) m/z 388 (30, M$^+$), 370 (2, M$^+$—H$_2$O), 322 (4, M$^+$-2 H$_2$O—C$_2$H$_6$), 303 (13), 287 (14, M$^+$—C$_6$H$_{13}$O), 269 (12, M$^+$—C$_6$H$_{13}$O—H$_2$O), 251 (10, M$^+$—C$_6$H$_{13}$O—2 H$_2$O), 235 (10), 186 (17), 155 (33), 135 (35), 114 (100), 91 (74); exact mass calculated for C$_{25}$H$_{40}$O$_3$ (M$^+$) 388.2977, found 388.2985.

(20S)-2α-methyl-19,26,27-trinor-1α,25-dihydroxy-calciferol (14) and (20S)-2β-methyl-19,26,27-trinor-1α,25-dihydroxycalciferol (15)

Tris(triphenylphosphine)rhodium (I) chloride (8 mg, 8.6 μmol) was added to dry benzene (8 mL) presaturated with hydrogen. The mixture was stirred at room temperature until a homogeneous solution was formed (ca. 45 minutes). A solution of vitamin 13 (3 mg, 7.7 μmol) in dry benzene (3 mL) was then added, and the reaction was allowed to proceed under a continuous stream of hydrogen for 8 hours. Benzene was removed under vacuum, and the residue was redissolved in hexane/ethyl acetate (1:1) and applied on a Waters silica Sep-Pak cartridge (2 g). A mixture of the 2-methyl vitamins was eluted using the same solvent system. The compounds were further purified by HPLC (9.4× 250 mm Zorbax-Sil column, 6 mL/min) using a hexane/2-propanol (85:15) solvent system. The mixture of 2-methyl-19-norvitamins 14 and 15 gave a single peak at $R_t$=7.4 min. Separation of both epimers was achieved using reversed-phase HPLC (9.4×250 mm Zorbax Eclipse XDB-C18 column, 3 mL/min) using a methanol/water (85:15) solvent system. 2β-Methyl vitamin 15 (456 μg, 15% yield) was collected at $R_t$=7.7 minutes, and its 2α-epimer 14 (505 μg, 17% yield) was collected at $R_t$=10.6 minutes 2α-Methyl analog 14: UV (in EtOH) $\lambda_{max}$ 260.0, 250.1, 241.9 nm; $^1$H NMR (500 MHz, CDCl$_3$) δ 6.36 and 5.82 (1H and 1H, each d, J=11.3 Hz, 6- and 7-H), 3.96 (1H, m, 1β-H), 3.62 (3H, m, 3α-H and 25-H$_2$), 2.80 (2H, br m, 9β- and 10α-H), 2.60 (1H, dd, J=12.8, 4.3 Hz, 4α-H), 2.22 (1H, br d, J=13.6 Hz, 10β-H), 2.13 (1H, ~t, J~11.3 Hz, 4β-H), 1.132 (3H, d, J=6.8 Hz, 2α-CH$_3$), 0.842 (3H, d, J=6.5 Hz, 21-H$_3$), 0.530 (3H, s, 18-H$_3$); MS (EI) m/z 390 (100, M$^+$), 372 (8, M$^+$—H$_2$O), 357 (3, M$^+$—H$_2$O—CH$_3$), 339 (5, M$^+$-2H$_2$O—CH$_3$), 317 (12, M$^+$—C$_4$H$_8$OH), 289 (39, M$^+$—C$_6$H$_{12}$OH), 271 (23, M$^+$—C$_6$H$_{12}$OH—H$_2$O), 235 (37), 194 (23), 177 (43), 135 (68), 95 (74); exact mass calculated for C$_{25}$H$_{42}$O$_3$ (M$^+$) 390.3134, found 390.3135.

2β-Methyl analog 15: UV (in EtOH) $\lambda_{max}$ 260.0, 249.9, 241.8 nm; $^1$H NMR (500 MHz, CDCl$_3$) δ 6.25 and 5.87 (1H and 1H, each d, J=11.1 Hz, 6-H and 7-H), 3.89 (1H, m, 3α-H), 3.64 (2H, dd, J=12.1, 6.3 Hz, 25-H$_2$), 3.50 (1H, m, 1β-H), 3.08 (1H, dd, J=12.9, 4.0 Hz, 10β-H), 2.80 (1H, dd, J=12.0, 4.3 Hz, 9β-H), 2.43 (1H, br d, J=ca. 13.6 Hz, 4α-H), 2.34 (1H, dd, J=13.5, 2.8 Hz, 4β-H), 1.142 (3H, d, J=6.8 Hz, 2β-CH$_3$), 0.847 (3H, d, J=6.5 Hz, 21-H$_3$), 0.542 (3H, s, 18-H$_3$); MS (EI) m/z 390 (72, M$^+$), 372 (8, M$^+$—H$_2$O), 354 (3, M$^+$-2H$_2$O), 339 (10, M$^{30}$ -2H$_2$O—CH$_3$), 317 (14, M$^+$—C$_4$H$_8$OH), 297 (40, M$^+$-2H$_2$O—C$_4$H$_9$), 289 (42, M$^+$—C$_6$H$_{12}$OH), 271 (26, M$^+$—C$_6$H$_{12}$OH—H$_2$O), 235 (32), 194 (31), 177 (97), 135 (99), 95 (100); exact mass calculated for C$_{25}$H$_{42}$O$_3$ (M$^+$) 390.3134, found 390.3119.

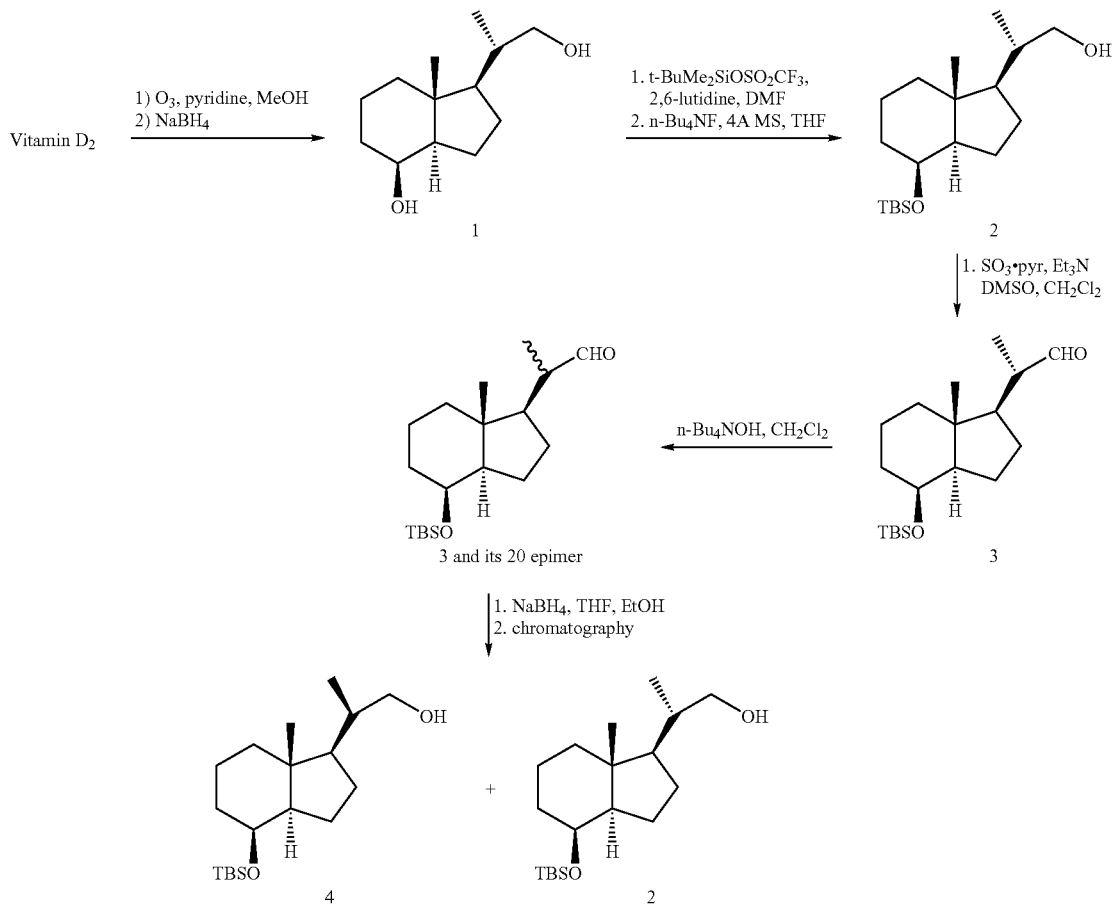

Scheme IIA

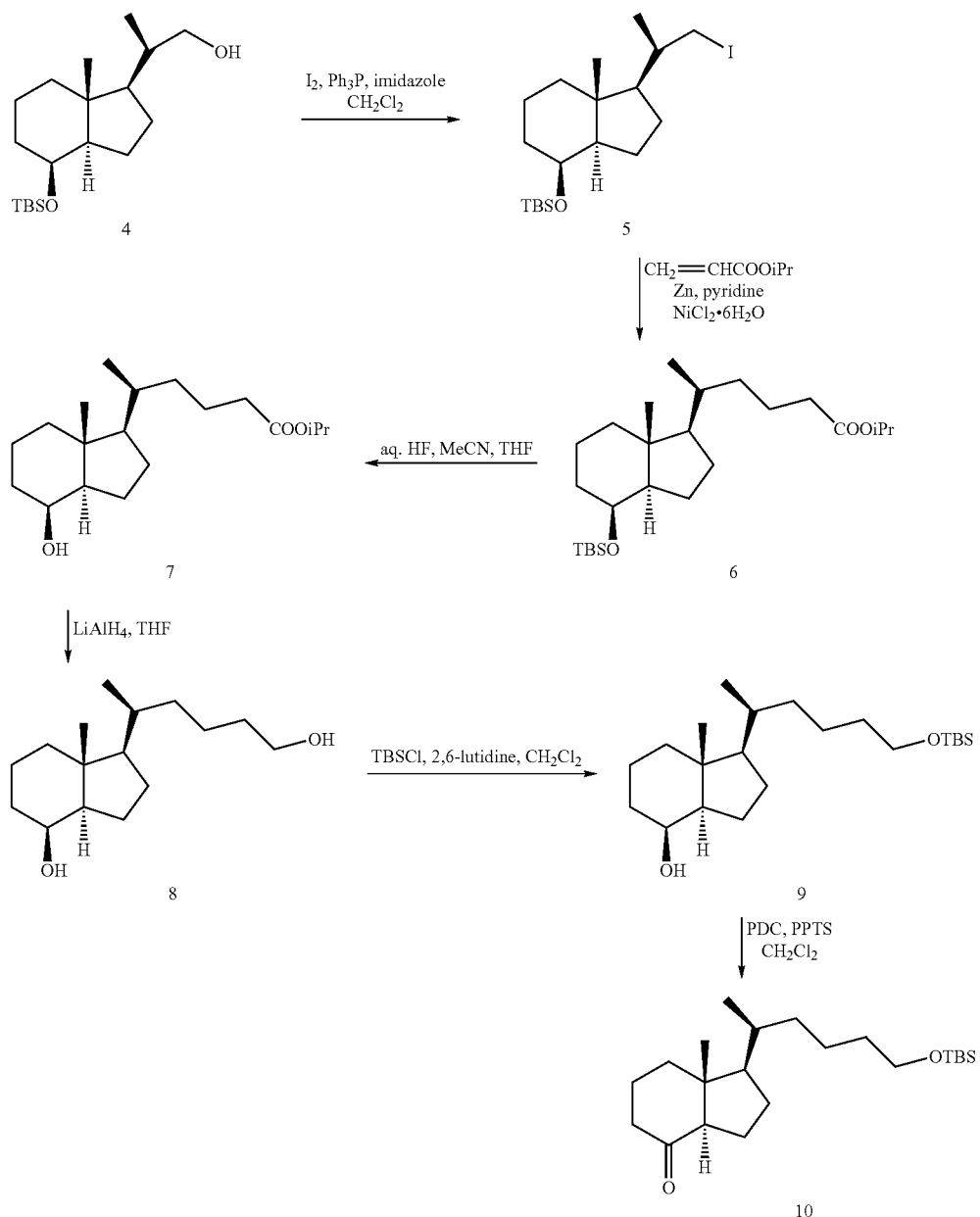
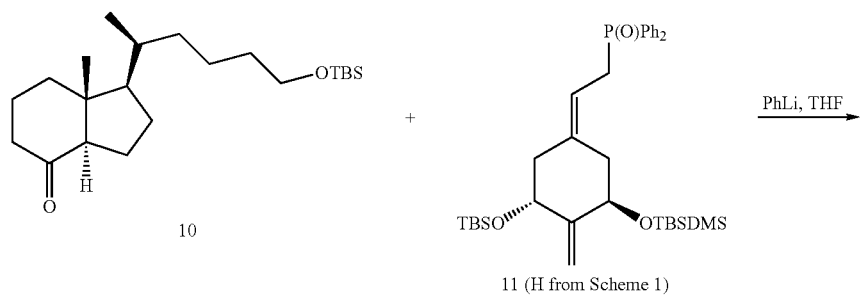

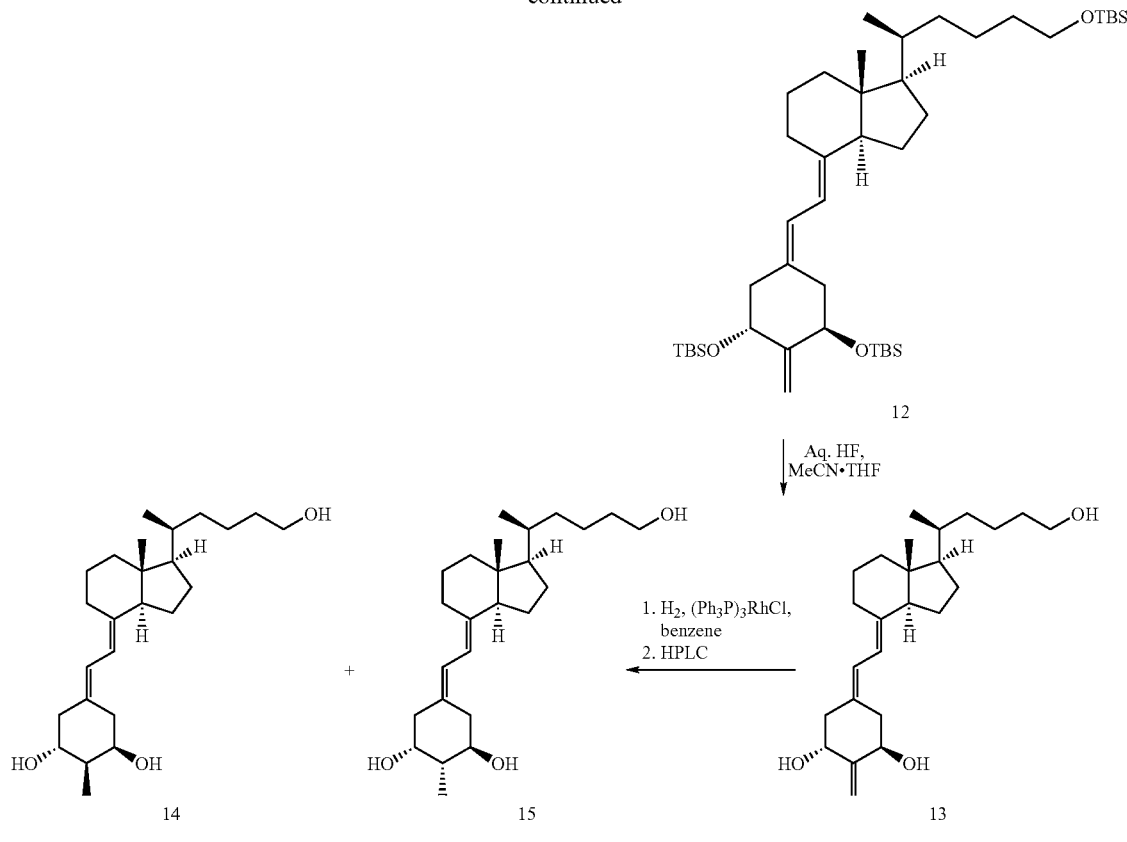

BIOLOGICAL ACTIVITY

Vitamin D Receptor Binding

Test Material

Protein Source

Full-length recombinant rat receptor was expressed in *E. coli* BL21(DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25(OH)$_2$D$_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25(OH)$_2$D$_3$, ~159 Ci/mmol) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapatite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 mL of Biosafe II scintillation cocktail, mixed and placed in a scintillation counter. Total binding was determined from the tubes containing only radiolabeled ligand.

HL-60 Differentiation

Test Material

Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at $1.2 \times 10^5$ cells/mL. Eighteen hours after plating, cells in duplicate were treated with drug. Four days later, the cells were harvested and a nitro blue tetrazolium reduction assay was performed (Collins et al., 1979; *J. Exp. Med.* 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (Suda et al. *J. Nutr.* 100:1049, 1970) (0.47% Ca) diet+vitamins AEK for one week followed by Diet 11 (0.02% Ca)+AEK for 3 weeks. The rats were then switched to a diet containing 0.47% Ca for one week followed by two weeks on the diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Figure 2:
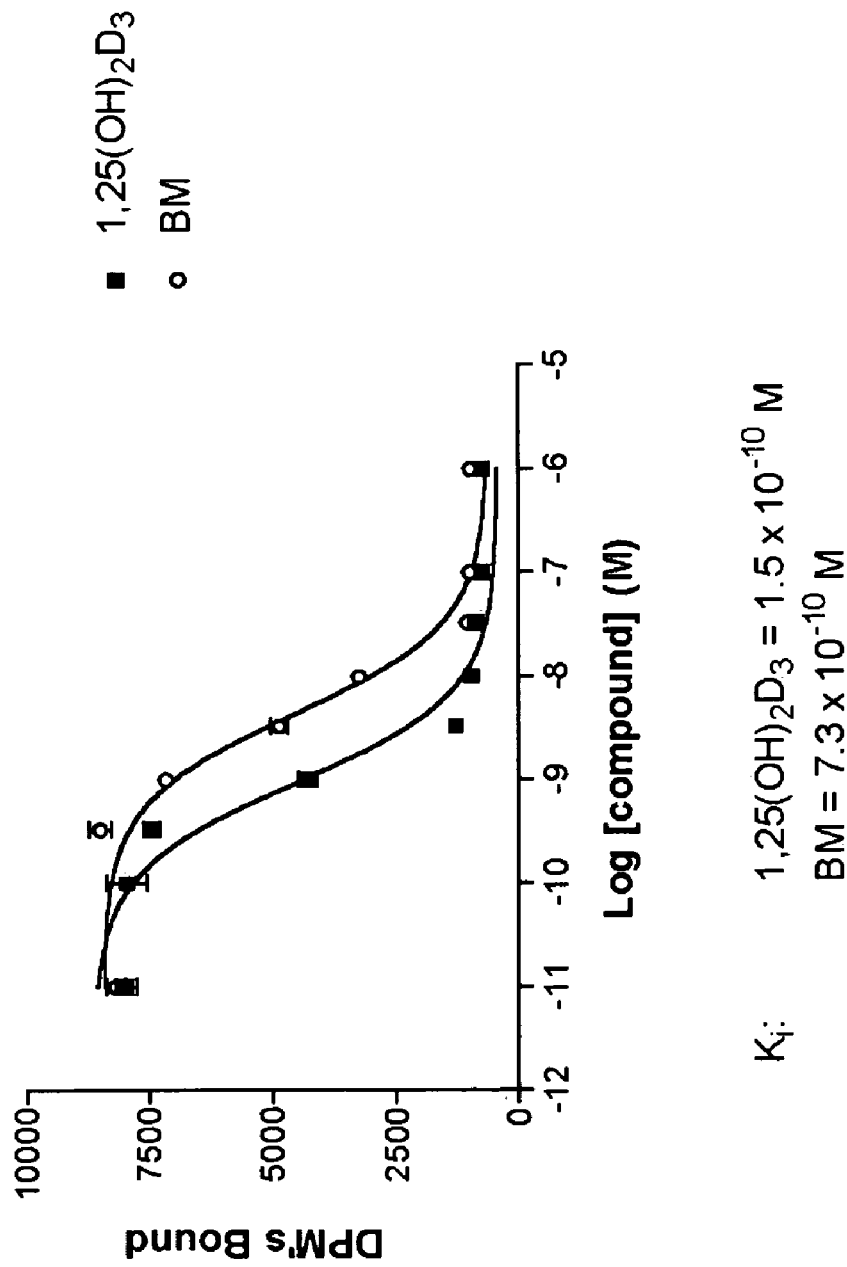
Figure 3:
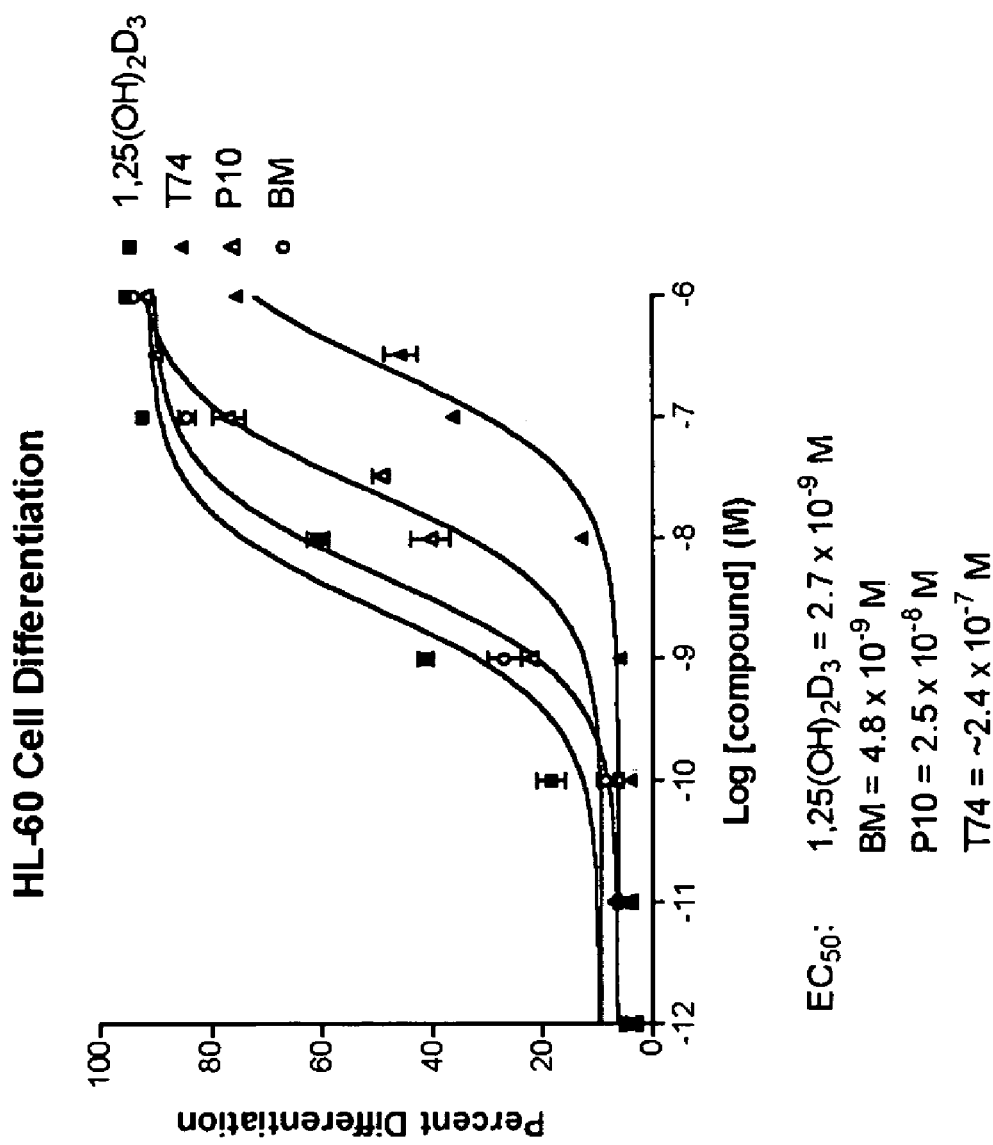
Figure 4:
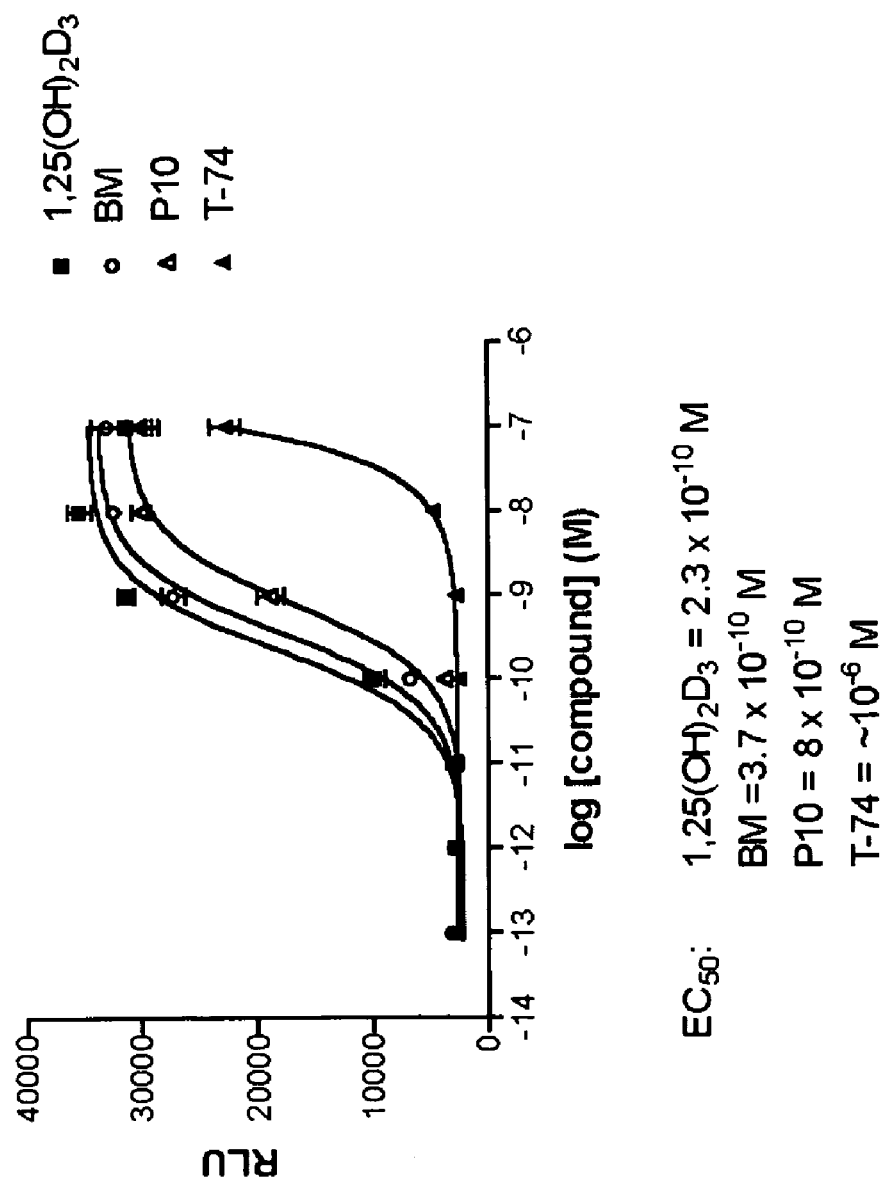
Figure 5:
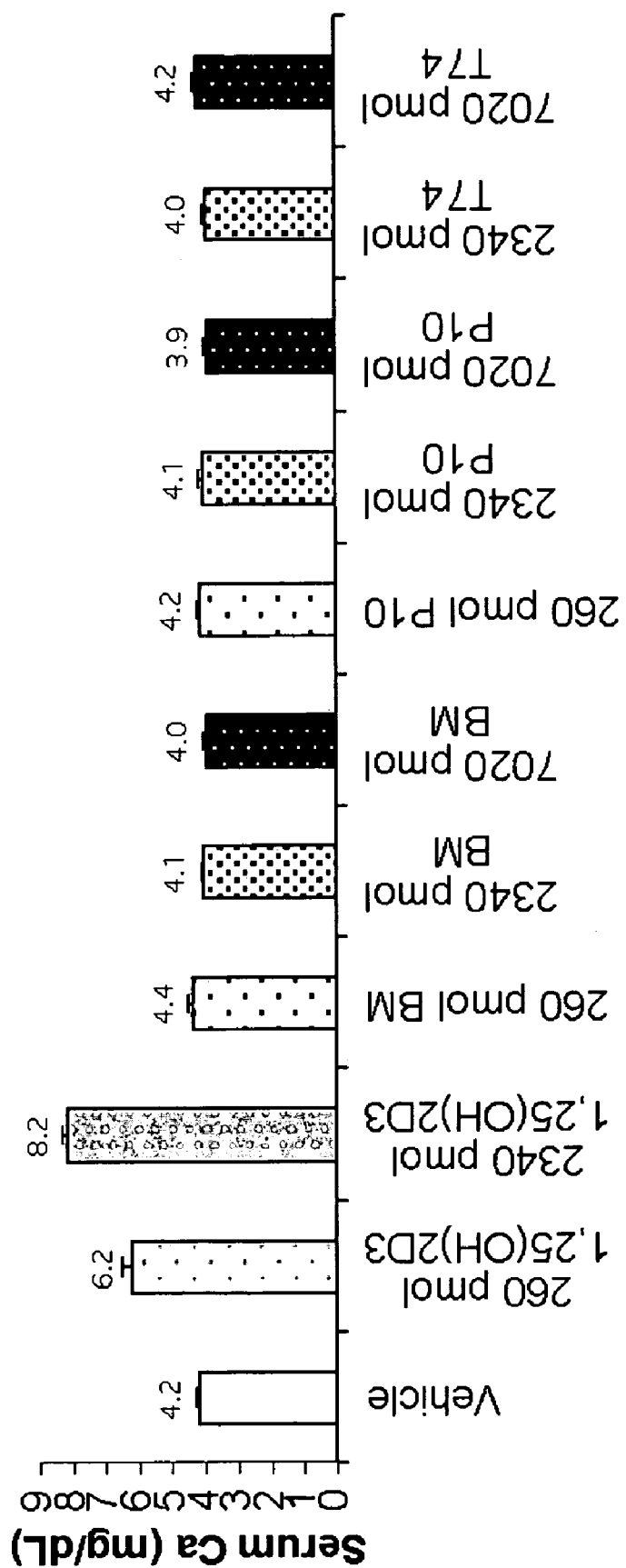
Figure 6:
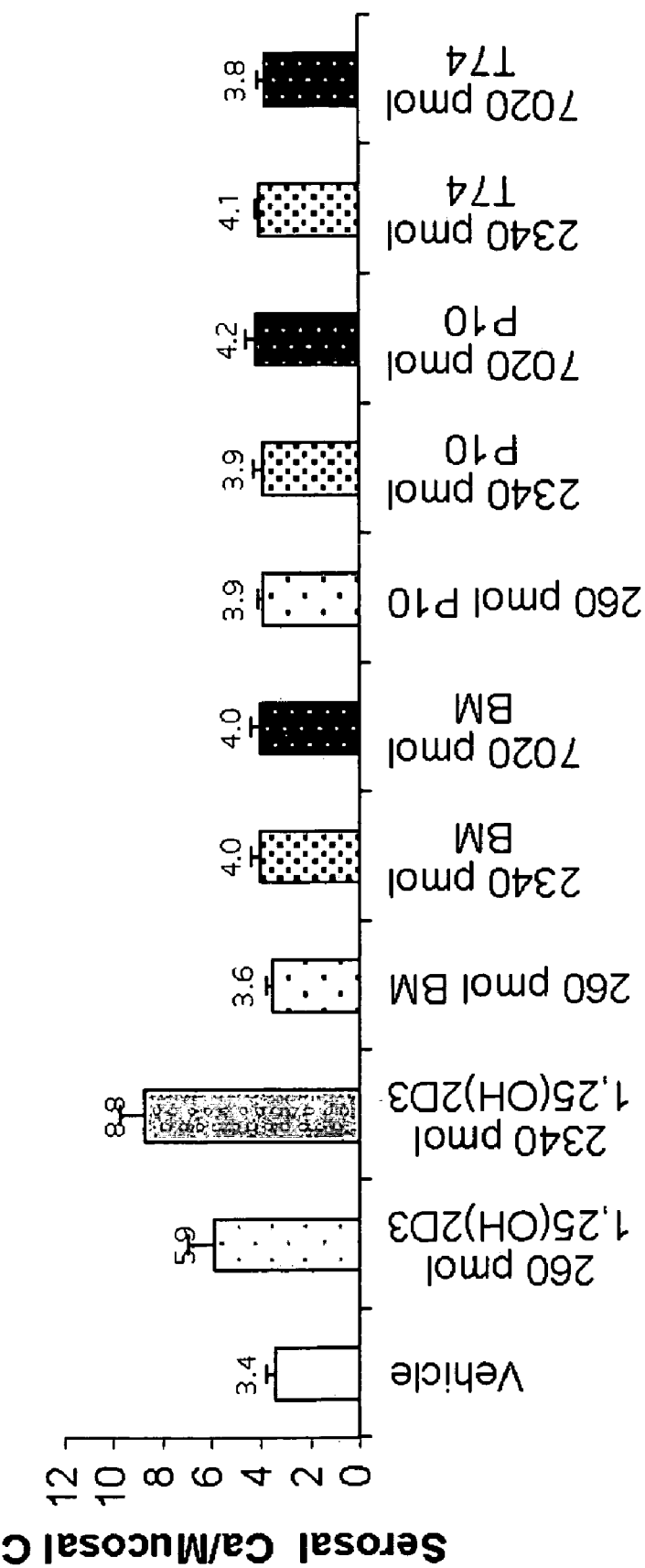
Figure 7:
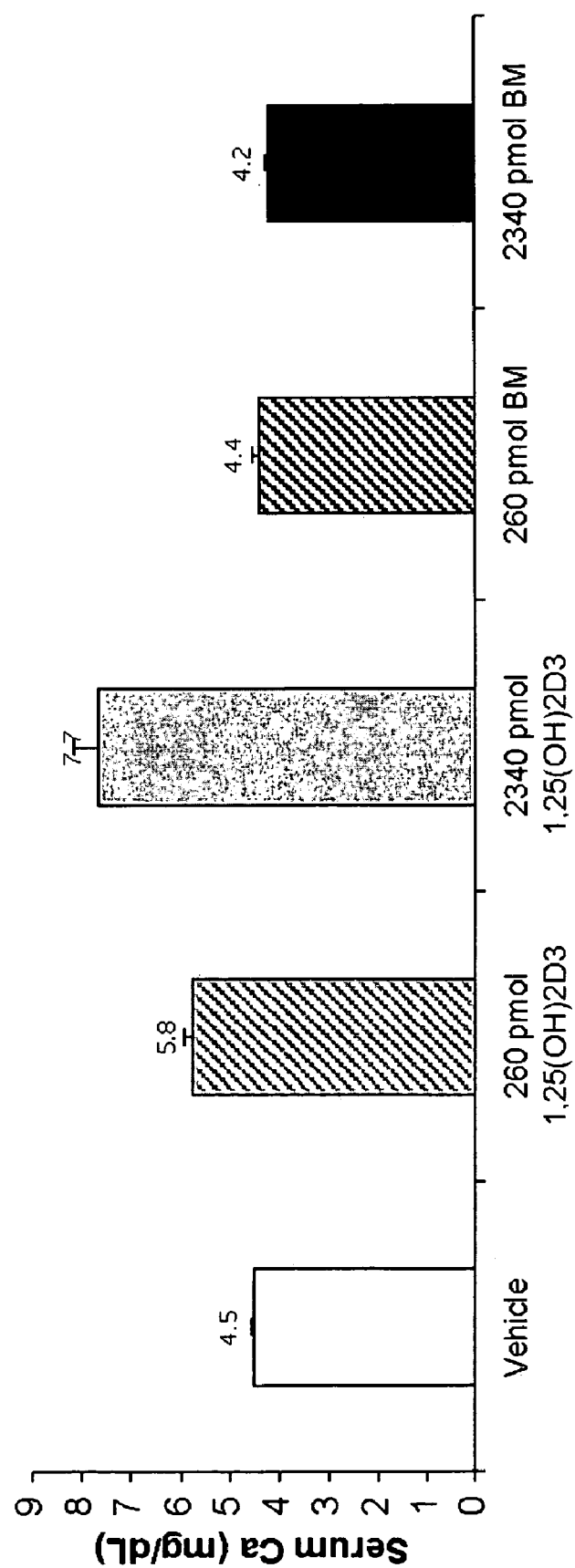
Figure 8:
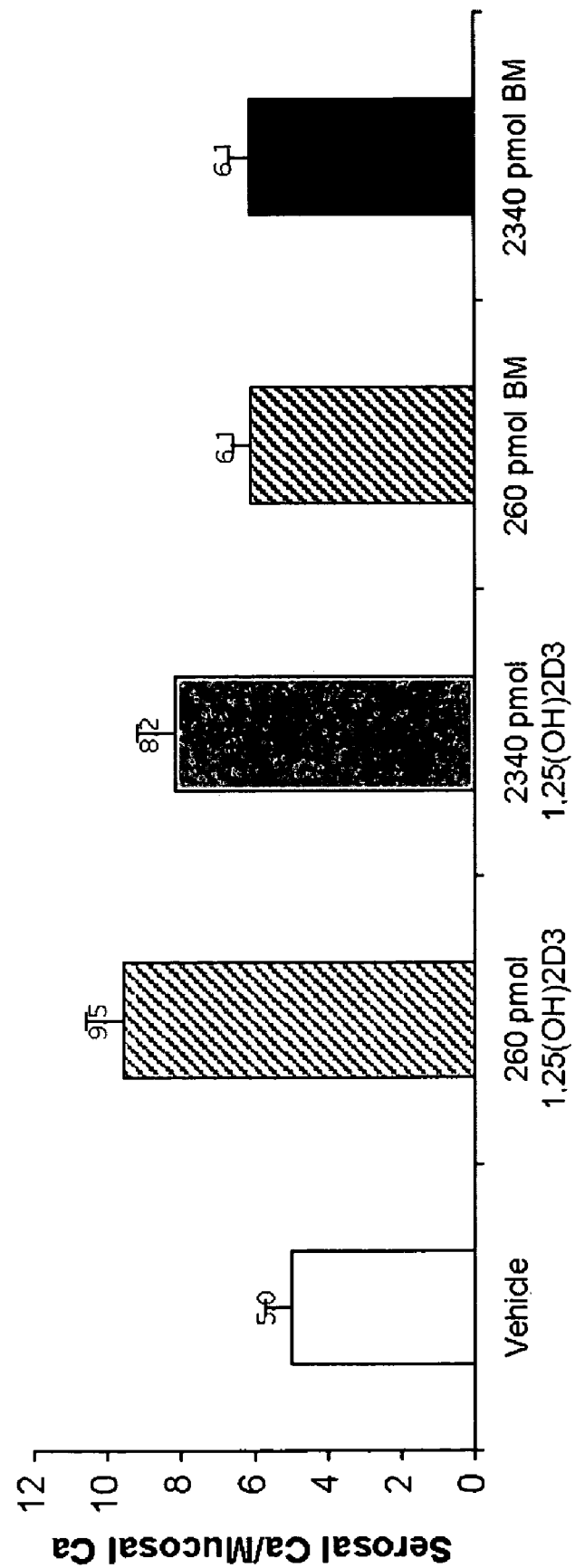

Both P10 and T-74 bind to the vitamin D receptor. While P10 is slightly more active than is $1\alpha,25$-dihydroxyvitamin $D_3$ in binding to the vitamin D receptor, T-74 is less active (see FIG. 1). BM also binds to the vitamin D receptor, but is slightly less active in this respect than is $1\alpha,25$-dihydroxyvitamin $D_3$ (see FIG. 2). P10, T-74, and BM also show less activity than $1\alpha,25$-dihydroxyvitamin $D_3$ in inducing differentiation of HL-60 cells (FIG. 3). However, BM is only slightly less active that $1\alpha,25$-dihydroxyvitamin $D_3$ in inducing differentiation of HL-60 cells. BM and P10 have slightly less activity than $1\alpha,25$-dihydroxyvitamin $D_3$ in causing transcription, and T-74 has significantly less activity than $1\alpha,25$-dihydroxyvitamin $D_3$ in this respect as shown in FIG. 4. P10, T-74, and BM have no calcemic activity when measured by bone calcium mobilization even when given at the dose of 7,020 pmol/day (see FIGS. 5 and 7). P10, T-74, and BM also do not elevate intestinal calcium transport (see FIGS. 6 and 8). These compounds may thus find use in therapies for treating diseases where a rise in serum calcium is not desirable. Examples of such diseases include, but are not limited to, renal osteodystrophy, psoriasis, type I diabetes, rheumatoid arthritis, lupus, leukemia, colorectal cancer, prostate cancer, and breast cancer. T-74 may find use as a cosmetic agent or cosmetic to treat sun-damaged skin, eliminate wrinkles or as a barrier enhancer to increase skin hydration.

For treatment purposes, the compounds of the invention may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically acceptable and non-toxic excipients such as stabilizers, anti-oxidants, binders, coloring agents or emulsifying or taste-modifying agents. Pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is hereby incorporated by reference in its entirety and for all purposes as if fully set forth herein.

The compounds may be administered orally, topically, parenterally, rectally, or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. In some embodiments, doses of from 0.001 μg to about 1 mg per day of the compound are appropriate for treatment purposes. In some such embodiments an appropriate and effective dose may range from 0.01 μg to 1 mg per day of the compound. In other such embodiments an appropriate and effective dose may range from 0.1 μg to 500 μg per day of the compound. Such doses will be adjusted according to the type of disease or condition to be treated, the severity of the disease or condition, and the response of the subject as is well understood in the art. The compound may be suitably administered alone, or together with another active vitamin D compound.

Compositions for use in the invention include an effective amount of P10, T-74, and/or BM as the active ingredient or ingredients, and a suitable carrier. An effective amount of the compound or compounds for use in accordance with some embodiments of the invention will generally be a dosage amount such as those described herein, and may be administered topically, transdermally, orally, nasally, rectally, or parenterally.

The compounds of the invention may be advantageously administered to a subject in amounts sufficient to effect the differentiation of promyelocytes to normal macrophages, i.e., in amounts sufficient to reduce the subject's level of promyelocytes below the level existing prior to administration. Dosages as described above are suitable, it being understood that the amounts given are to be adjusted in accordance with the severity of the disease, and the condition and response of the subject as is well understood in the art. As noted, the compounds of the invention may be used in a purified form or may be present as a mixture. For examples, compounds of formula 3A and formula 3B may be present as a mixture of the two compounds. In some embodiments, the mixture includes the compound of formula 3A and the compound of formula 3B, and the ratio of the compound of formula 3A to the compound of formula 3B ranges from 50:50 to 99.9:0.1. In some such embodiments, the ratio of the compound of formula 3A to the compound of formula 3B ranges from 70:30 to 99.9:0.1, from 80:20 to 99.9:0.1, from 90:10 to 99.9:0.1, or from 95:5 to 99.9:0.1. In other embodiments, the mixture includes the compound of formula 3A and the compound of formula 3B, and the ratio of the compound of formula 3B to the compound of formula 3A ranges from 50:50 to 99.9:0.1. In some such embodiments, the ratio of the compound of formula 3B to the compound of formula 3A ranges from 70:30 to 99.9:0.1, from 80:20 to 99.9:0.1, from 90:10 to 99.9:0.1, or from 95:5 to 99.9:0.1.

The compound or compounds may be formulated as creams, lotions, ointments, aerosols, suppositories, topical patches, pills, capsules or tablets, or in liquid form as solutions, emulsions, dispersions, or suspensions in pharmaceutically innocuous and acceptable solvent(s) or oil(s), and such preparations may contain, in addition, other pharmaceutically innocuous or beneficial components, such as stabilizers, antioxidants, emulsifiers, coloring agents, binders or taste-modifying agents.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100 microns.

The formulations may conveniently be presented in dosage unit form and may be prepared by any of the methods well known in the art of pharmacy. By the term "dosage unit" is meant a unitary, i.e., a single dose, which is capable of being administered to a patient as a physically and chemically stable unit dose comprising either the active ingredient as such or a mixture of it with solid or liquid pharmaceutical diluents or carriers.

All references cited herein are specifically incorporated by reference in their entireties and for all purposes as if fully set forth herein.

It is understood that the invention is not limited to the embodiments set forth herein for illustration, but embraces all such forms thereof as come within the scope of the following claims.

What is claimed is:

1. A compound having the formula 1,

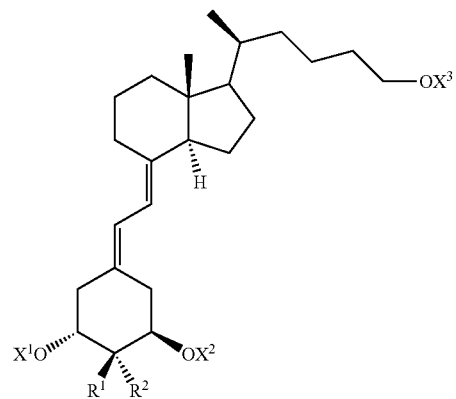

wherein, $X^1$, $X^2$, and $X^3$ are independently selected from H or hydroxy protecting groups; and $R^1$ and $R^2$ are independently selected from H or straight or branched chain alkyl groups having from 1 to 8 carbon atoms; or $R^1$ and $R^2$ join together to form a group of formula 2

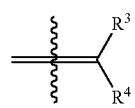

where the wavy line indicates the point of attachment to the carbon at the 2 position of the vitamin D analog, and $R^3$ and $R^4$ are independently selected from H or straight or branched chain alkyl groups having from 1 to 8 carbon atoms.

2. The compound of claim 1, wherein $X^3$ is H, and the compound of formula 1 has the formula 1A

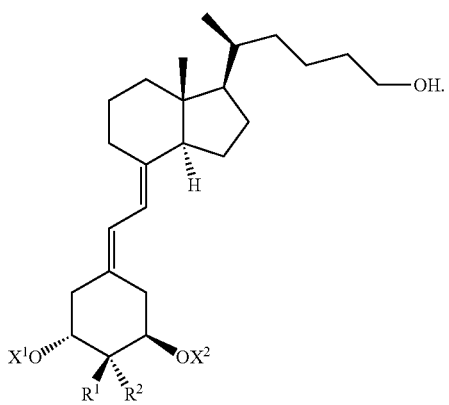

3. The compound of claim 2, wherein $X^1$ and $X^2$ are both hydroxy protecting groups.

4. The compound of claim 3, wherein $X^1$ and $X^2$ are both t-butyldimethylsilyl groups.

5. The compound of claim 2, wherein $X^1$ and $X^2$ are both H and the compound has the formula 3A

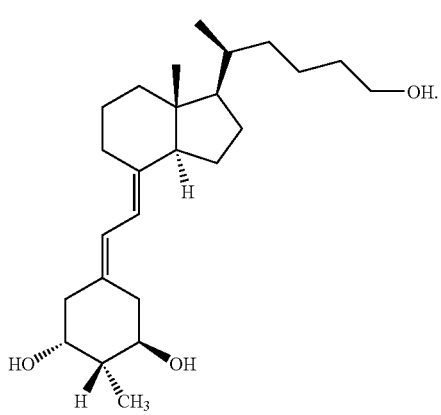

6. The compound of claim 2, wherein $X^1$ and $X^2$ are both H and the compound has the formula 3B

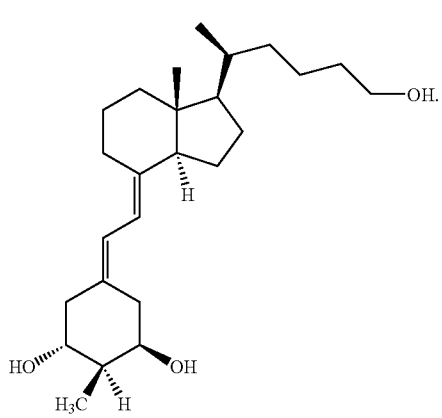

7. The compound of claim 2, wherein $X^1$ and $X^2$ are both H and the compound has the formula 3C

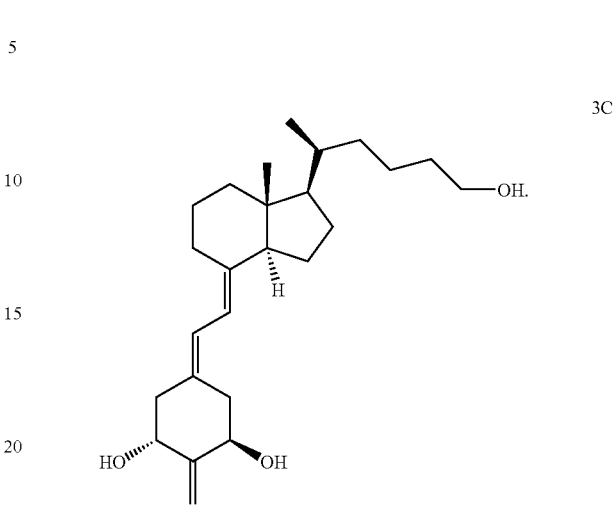

8. A pharmaceutical composition, comprising an effective amount of the compound of claim 1 and a pharmaceutically acceptable carrier.

9. The pharmaceutical composition of claim 8, wherein the effective amount comprises from about 0.01 μg to about 1 mg of the compound per gram of the composition.

10. The pharmaceutical composition of claim 9, wherein the effective amount comprises from about 0.1 μg to about 500 μg of the compound per gram of the composition.

11. The pharmaceutical composition of claim 8, wherein $X^3$ is H.

12. The pharmaceutical composition of claim 11, wherein $X^1$ and $X^2$ are both H.

* * * * *

UNITED STATES PATENT AND TRADEMARK OFFICE
CERTIFICATE OF CORRECTION

PATENT NO. : 7,241,909 B2 Page 1 of 1
APPLICATION NO. : 11/416401
DATED : July 10, 2007
INVENTOR(S) : Hector F. DeLuca et al.

It is certified that error appears in the above-identified patent and that said Letters Patent is hereby corrected as shown below:

<u>Col. 7, line 23:</u>

Delete "2α-methyl-19," and replace it with --2β-methyl-19,--.

<u>Col. 18, line 46:</u>

Delete "ml/min," and replace with --mL/min,--.

<u>Col. 20, line 23:</u>

Replace "(10, $M^{30}$ -2H$_2$O-CH$_3$)" with --(10, $M^+$ -2H$_2$O-CH$_3$)--.

Signed and Sealed this

Twenty-ninth Day of April, 2008

JON W. DUDAS
*Director of the United States Patent and Trademark Office*